United States Patent [19]
Kimura et al.

[11] Patent Number: 5,695,448
[45] Date of Patent: Dec. 9, 1997

[54] ENDOSCOPIC SHEATH

[75] Inventors: Shuichi Kimura, Hino; Toshiya Sugai, Hachioji, both of Japan

[73] Assignee: Olympus Optical Co., Ltd., Tokyo, Japan

[21] Appl. No.: 519,481

[22] Filed: Aug. 25, 1995

[30] Foreign Application Priority Data

| Aug. 29, 1994 | [JP] | Japan | 6-203639 |
| Jul. 7, 1995 | [JP] | Japan | 7-172466 |

[51] Int. Cl.$^6$ ................................ A61B 1/04
[52] U.S. Cl. ................ 600/121; 600/114; 600/124; 600/125; 600/129
[58] Field of Search ................ 600/121, 123, 600/124, 125, 127, 128, 129, 186, 116, 114, 115, 203

[56] References Cited

U.S. PATENT DOCUMENTS

| 4,779,611 | 10/1988 | Grooters et al. | 600/116 |
| 4,807,593 | 2/1989 | Ito | 600/114 |
| 4,878,485 | 11/1989 | Adair | 600/125 X |
| 5,154,166 | 10/1992 | Chikama | 600/125 X |
| 5,329,935 | 7/1994 | Takahashi | 600/121 |
| 5,415,157 | 5/1995 | Welcome | 600/121 |

FOREIGN PATENT DOCUMENTS

| 37 43 042 A1 | 4/1989 | Germany. |
| 4-10328 | 2/1992 | Japan. |
| 4-43202 | 10/1992 | Japan. |

Primary Examiner—Beverly M. Flanagan
Attorney, Agent, or Firm—Frishauf, Holtz, Goodman, Langer & Chick

[57] ABSTRACT

An endoscopic sheath of the present invention comprising a tubular sheath section having a distal end portion and a hole which extends throughout the length of the sheath section and through which an insert section of an endoscope having observation device can be passed, at least the distal end of the distal end portion opening, and at least the distal end portion being formed of a transparent material, and positioning device for positioning the insert section of the endoscope in the sheath section so that at least part of the distal end portion of the sheath section can be within the view range of the endoscope.

31 Claims, 23 Drawing Sheets

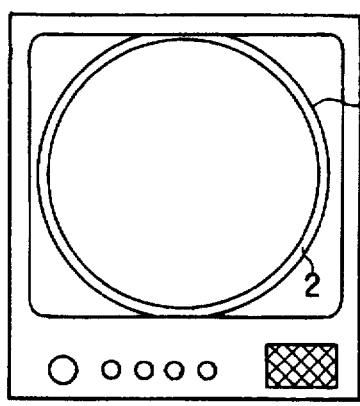
FIG. 3
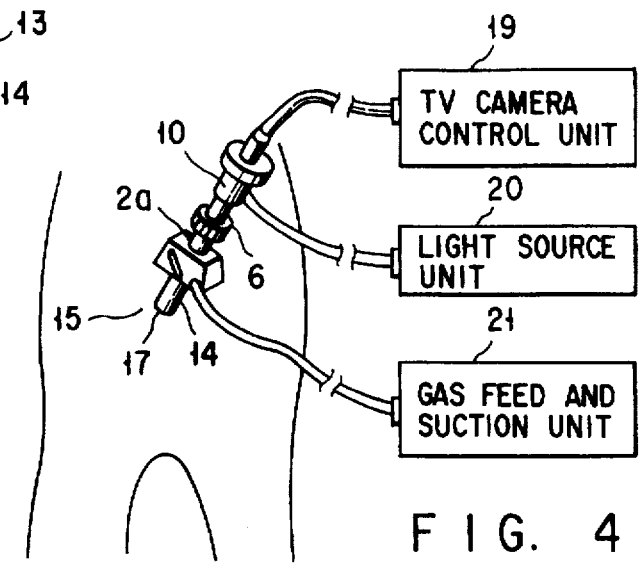
FIG. 4
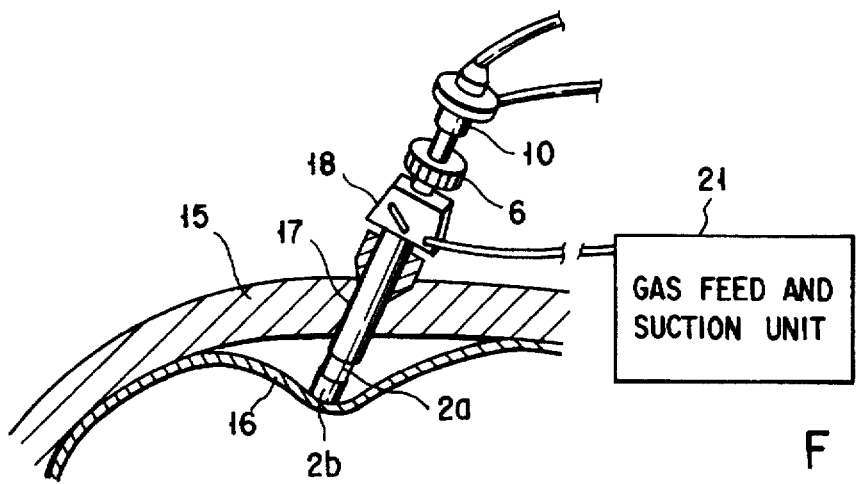
FIG. 5
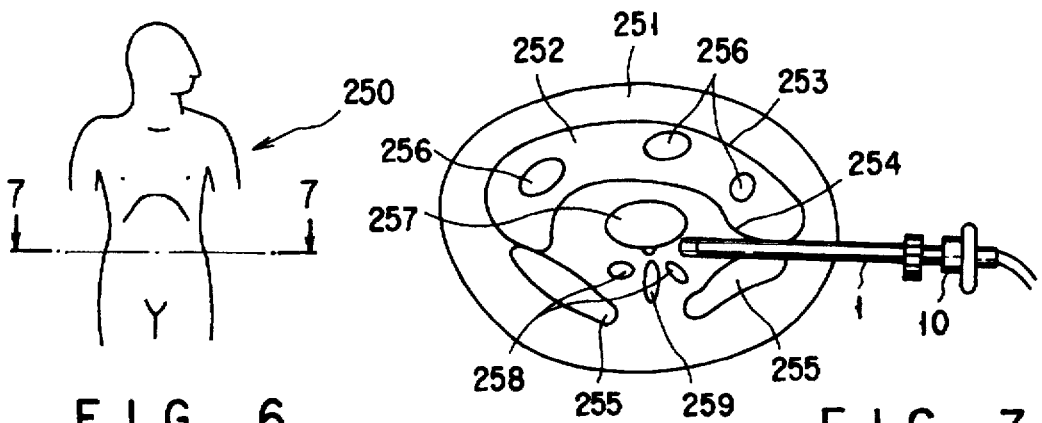
FIG. 6
FIG. 7

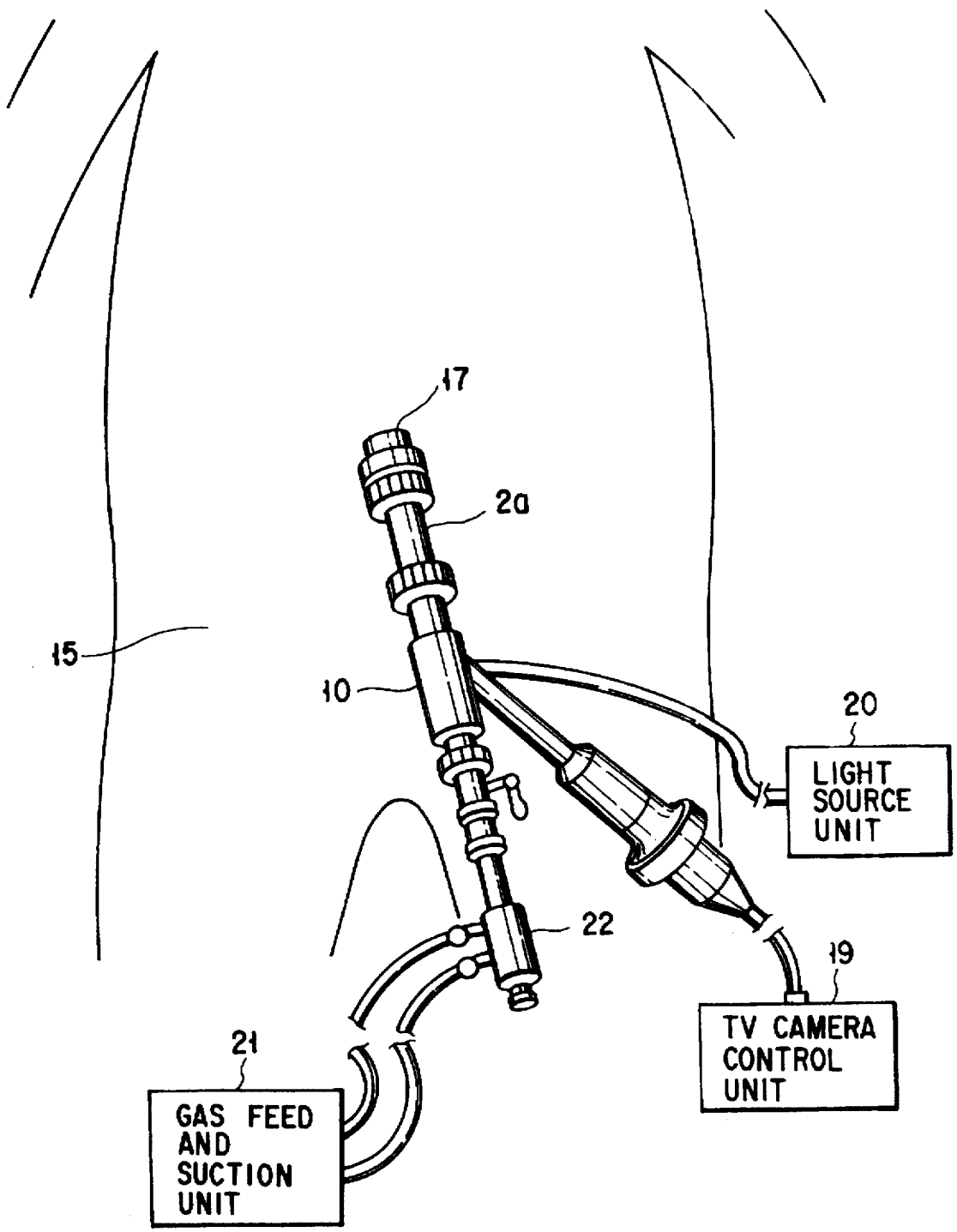
F I G. 8

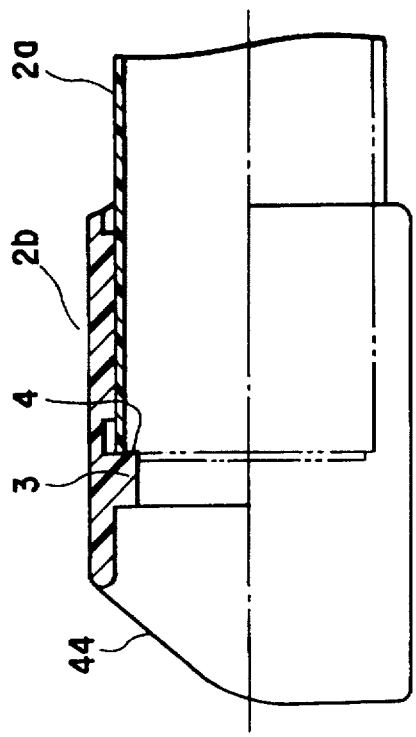
F I G. 14
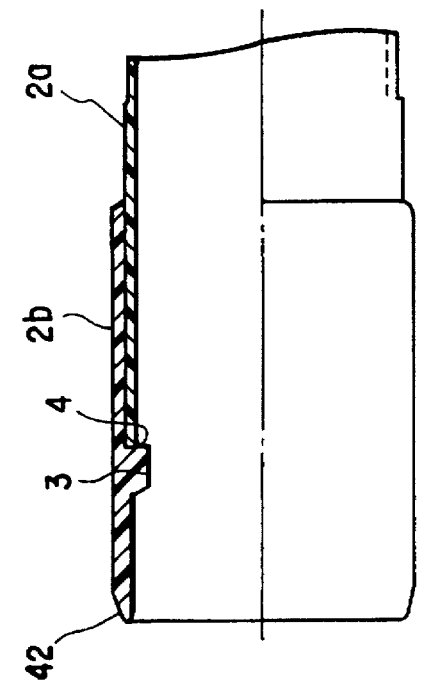
F I G. 13
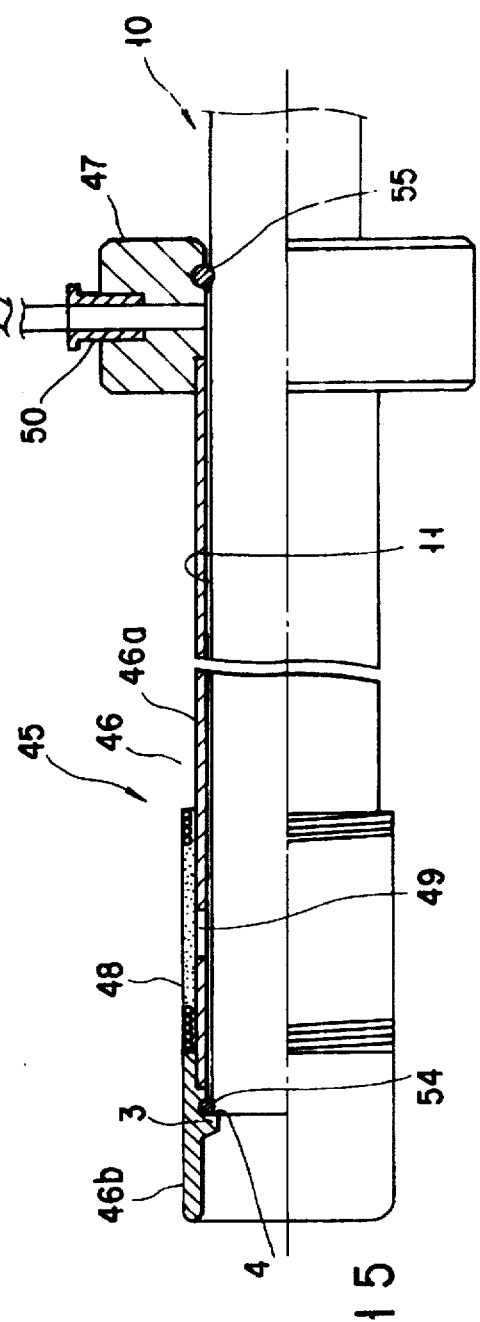
F I G. 15

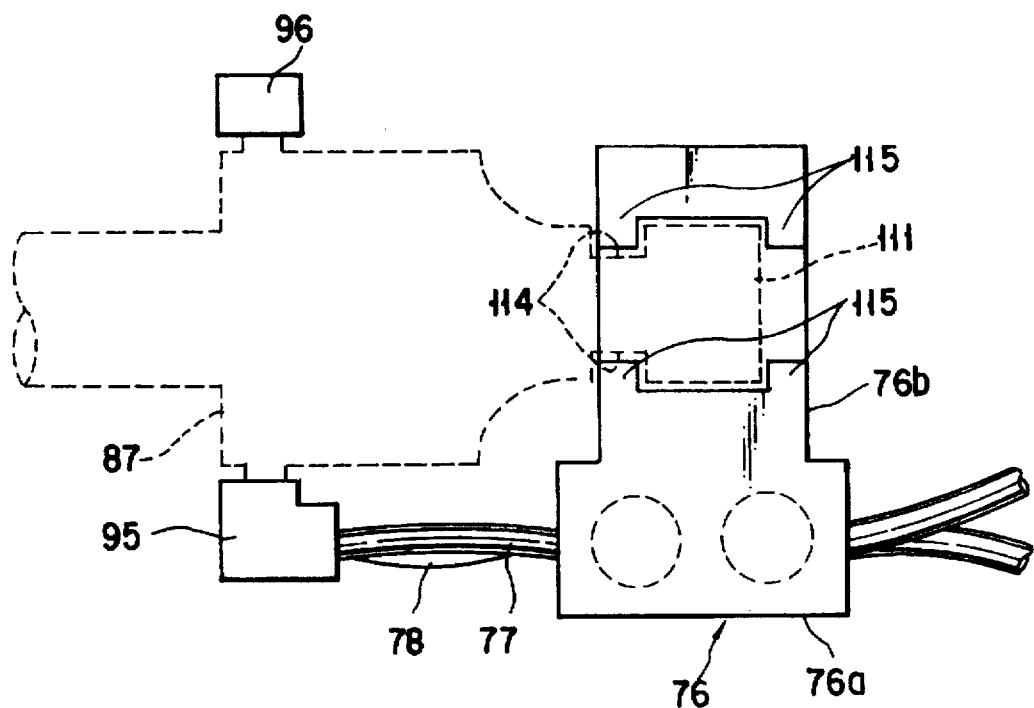
F I G. 27A
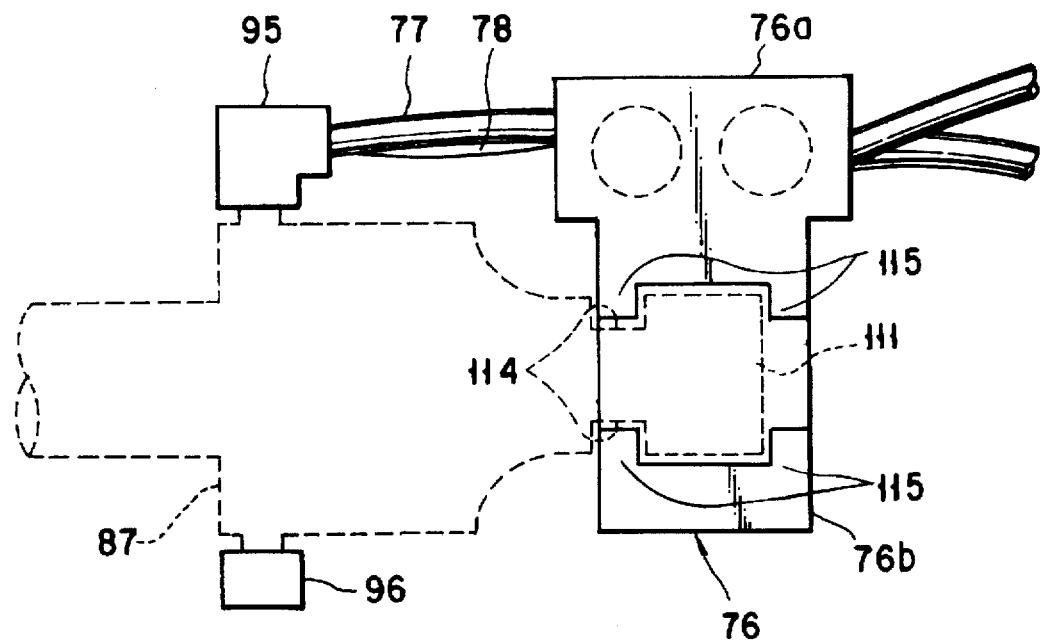
F I G. 27B

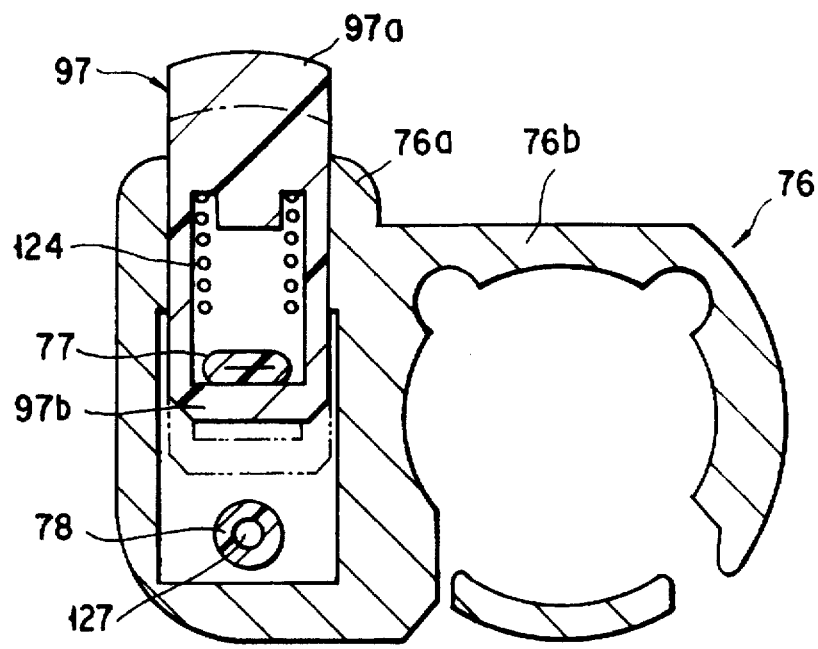
F I G. 29
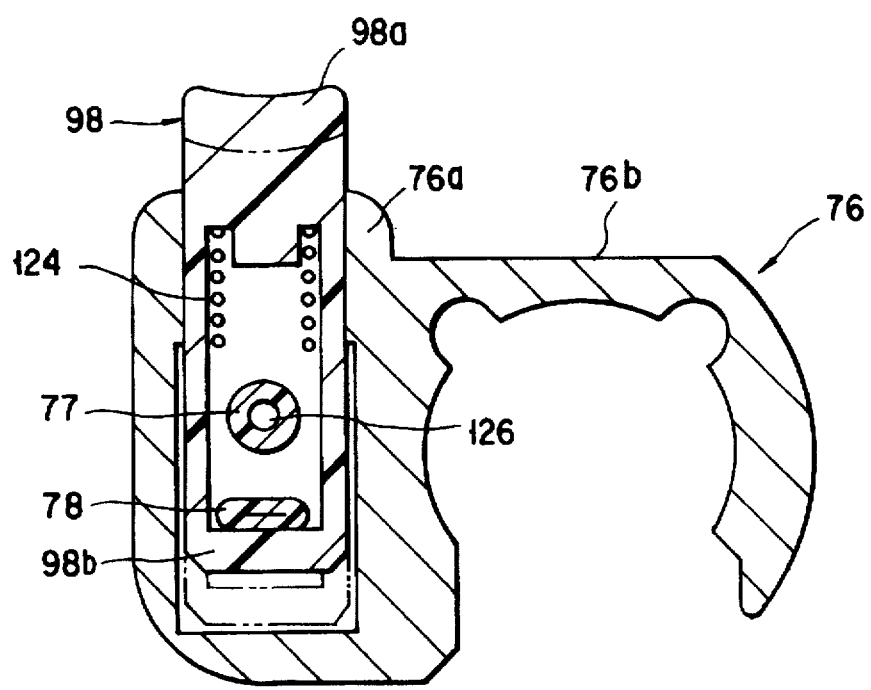
F I G. 30

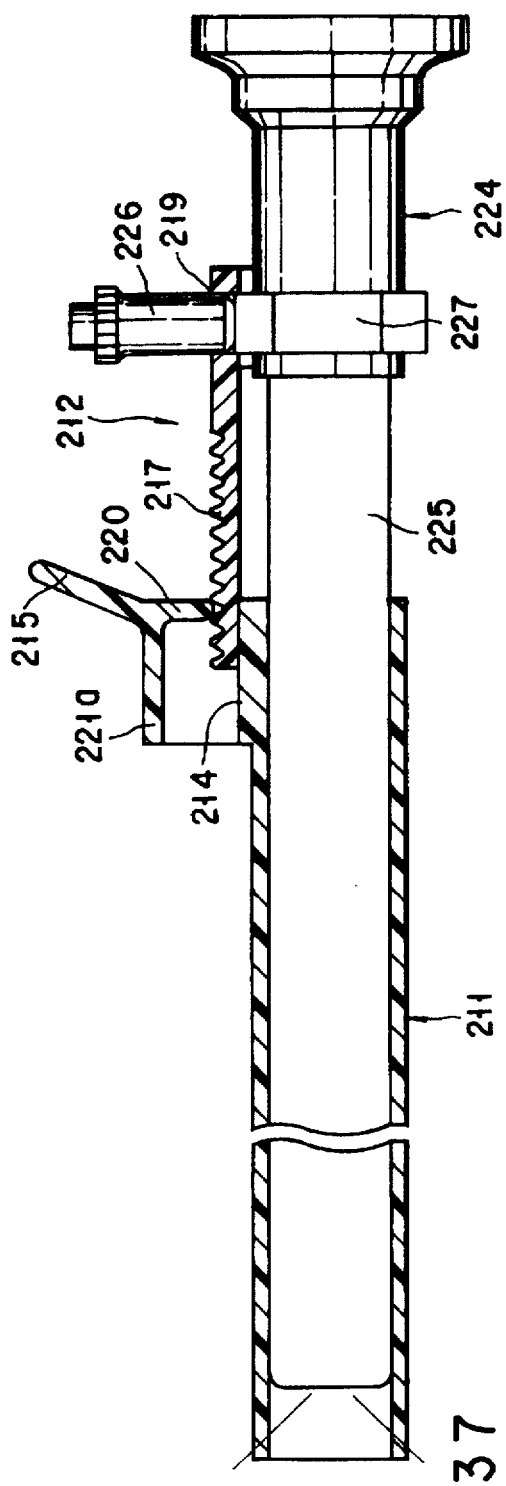
FIG. 37
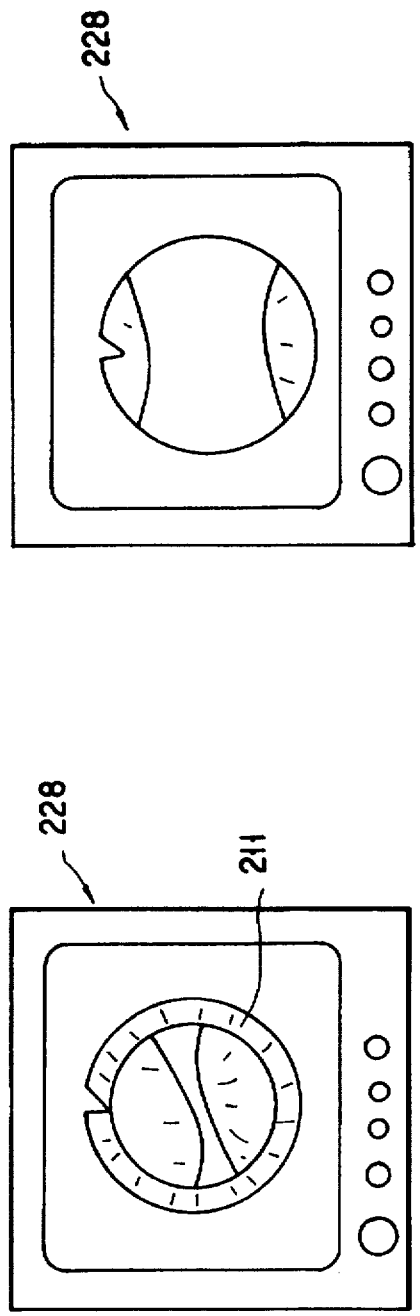
FIG. 39
FIG. 38

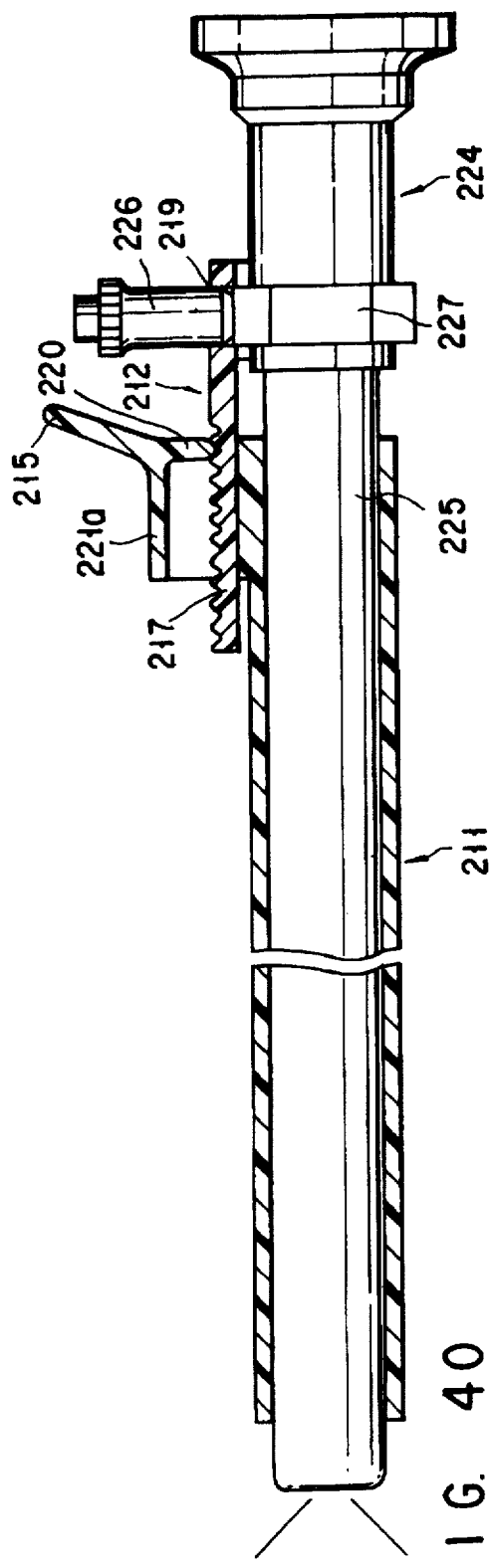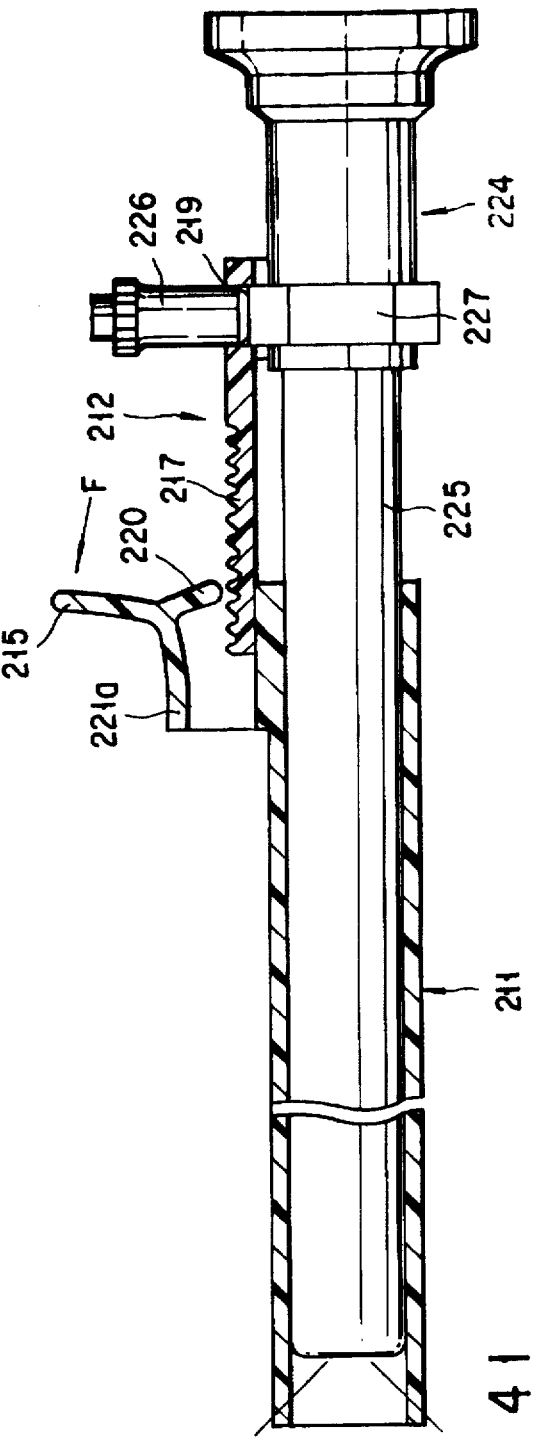
F I G. 40
F I G. 41

ENDOSCOPIC SHEATH

BACKGROUND OF THE INVENTION

1. Field of the Invention

The present invention relates to an endoscopic sheath used in combination with an endoscope for observing the interior of a body cavity.

2. Description of the Related Art

Conventional sheaths to be fitted on the insert section of endoscopes have various configurations depending on the purpose of application.

Described in Jpn. Pat. Appln. KOKOKU Publication No. 4-10328, for example, is a sheath which enables a direct endoscopic observation of subcutaneous tissue or any other desired portion of a living body in which no spaces exist. This sheath is a rigid guide tube through which an endoscope is passed and guided to a target region in a patient's body. The distal end of the sheath is closed, and at least part of it is formed of a material which transmits light. As this sheath is inserted into subcutaneous tissue or other organic portion without spaces, it thrusts aside the organic portion, thereby positively creating a space in the region. Thus, by passing the endoscope through the sheath kept in the subcutaneous tissue, for example, the tissue can be subjected to endoscopic observation through the transparent guide tube portion.

Disclosed in Jpn. UM Appln. KOKOKU Publication No. 4-43202, moreover, is a tubular protective sheath which is fitted on an insert section of an endoscope to protect the endoscope. This sheath enables endoscopic observation through its distal opening. A stopper for preventing projection of the endoscope is provided on that part of the distal end portion of the sheath which does not interfere with the view range of the endoscope. The stopper can prevent the endoscope from projecting from the distal end of the sheath without the possibility of the distal end edge of the sheath or the like interfering with the view range of the endoscope. Thus, the entire view range can be utilized, and the distal end portion of the endoscope can be prevented from being damaged.

The sheath used with the endoscope in this manner is expected to facilitate accurate observation of the state of a subject tissue by means of the endoscope, without interfering with the view range of the endoscope, and to be smoothly inserted together with the endoscope into a patient's body without injuring the patient.

Since the sheath described in Jpn. Pat. Appln. KOKOKU Publication No. 4-10328 is formed as a rigid body including the transparent portion for observation, however, the subject tissue is pressed by the sheath, so that it is hard to observe the color and shape of the tissue accurately. In case of bleeding, moreover, the pressure exerted on the subject tissue by the sheath makes the spot of bleeding obscure, making it appropriate treatment.

According to the arrangement described in Jpn. UM Appln. KOKOKU Publication No. 4-43202, on the other hand, the endoscopic observation of tissue can be achieved through the distal opening of the sheath, so that the subject tissue is not pressed by the sheath. Accordingly, this sheath is not subject to the aforesaid problems. Since the sheath cannot be situated within the view range of the endoscope, however, the degree of contact between the distal end portion of the sheath and the living tissue cannot be detected, so that the pressure of the sheath end portion on the tissue cannot be identified. Thus, the sheath cannot be smoothly inserted into a patient's body without injuring the patient.

SUMMARY OF THE INVENTION

The object of the present invention is to provide an endoscopic sheath, which enables a direct endoscopic observation of subcutaneous tissue or any other desired portion of a living body in which no spaces exist, facilitates accurate observation of the state of the subject tissue by means of an endoscope, without interfering with the view range of the endoscope, and can be smoothly inserted together with the endoscope into a patient's body without injuring the patient.

The above object is achieved by an endoscopic sheath constructed as follows. The endoscopic sheath comprises a tubular sheath section having a distal end portion and a hole which extends throughout the length of the sheath section and through which an insert section of an endoscope having observation means can be passed, at least the distal end of the distal end portion opening, and at least the distal end portion being formed of a transparent material; and positioning means for positioning the insert section of the endoscope in the sheath section so that at least part of the distal end portion of the sheath section is within the view range of the endoscope.

According to the endoscopic sheath constructed in this manner, tissues and the like can be observed through the distal opening of the tubular sheath section, so that a subject region to be observed through the opening cannot be pressed by the sheath section. Thus, the states (color, shape, etc.) of living tissue can be observed and grasped accurately.

Since at least part of the distal end portion of the sheath section enters the view range of the endoscope, the state of contact between the distal end portion of the sheath section and living tissue can be recognized with ease. Thus, the sheath section, along with the endoscope, can be smoothly inserted into a patient's body without injuring it, so that the safety and reliability of surgical operation can be improved.

In the arrangement described above, moreover, at least the distal end portion of the sheath section which enters the view range of the endoscope is formed from a transparent material in order to prevent the distal end portion of the sheath section from interfering with the view range. Even when the distal end portion of the sheath section enters the view range of the endoscope, therefore, living tissue can be observed through the transparent portion.

If the endoscopic sheath with the aforementioned construction is inserted into subcutaneous tissue or any other organism which has no spaces therein, it pushes aside this tissue or organism, thereby positively creating a space in the region. If the endoscope is passed through the sheath section which is inserted in the subcutaneous tissue, for example, therefore, the subcutaneous tissue can be subjected to endoscopic observation through the distal opening or transparent portion of the sheath section.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 3 is a front view showing an example of a monitor display of an image of an endoscope set in the endoscopic sheath of FIG. 1;

FIG. 4 is a view showing the way herniation is carried out by using the endoscopic sheath of FIG. 1;

FIG. 5 is a sectional view showing a process of herniation by means of the endoscopic sheath of FIG. 1;

FIG. 6 is a schematic view of a patient's body;

FIG. 7 is a sectional view taken along line 7—7 of FIG. 6;

FIG. 8 is a view showing the way appendectomy is carried out by using the endoscopic sheath of FIG. 1;

FIG. 13 is a sectional view showing the principal part of an endoscopic sheath according to a second embodiment of the invention;

FIG. 14 is a sectional view showing the principal part of an endoscopic sheath according to a third embodiment of the invention;

FIG. 15 is a half-sectional view showing an endoscopic sheath according to a fourth embodiment of the invention;

FIGS. 27A and 27B are plan views individually showing two examples of the way of mounting the valve unit of FIG. 26;

FIG. 29 is an enlarged sectional view taken along line 29—29 of FIG. 28;

FIG. 30 is an enlarged sectional view taken along line 30—30 of FIG. 28;

FIG. 37 is a longitudinal sectional view of the endoscopic sheath of FIG. 36;

FIG. 38 is a front view showing an example of a monitor display of an image of an endoscope set in the endoscopic sheath of FIG. 36;

FIG. 39 is a front view showing another example of the monitor display of the image of the endoscope set in the endoscopic sheath of FIG. 1;

FIG. 40 is a longitudinal sectional view of the endoscopic sheath of FIG. 36;

FIG. 41 is another longitudinal sectional view of the endoscopic sheath of FIG. 36;

DETAILED DESCRIPTION OF THE PREFERRED EMBODIMENTS

Preferred embodiments of the present invention will now be described with reference to the accompanying drawings.

Figure 1:
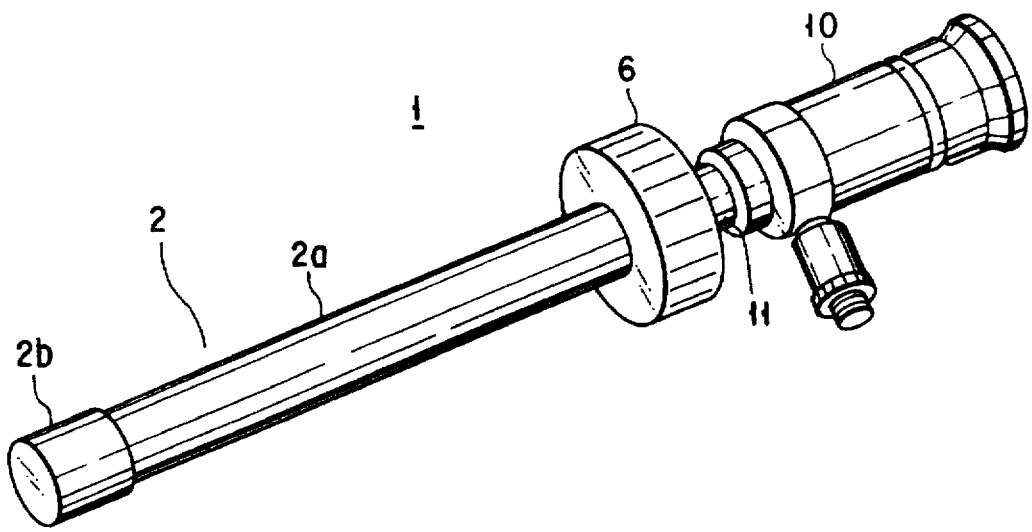
FIG. 1 is a perspective view of an endoscopic sheath according to a first embodiment of the present invention.

FIGS. 1 to 10 show a first embodiment of the present invention. As shown in FIG. 1, an endoscopic sheath 1 according to the present embodiment comprises a tubular sheath section 2 which can be inserted into a patient's body. The sheath section 2 is composed of a sheath body 2a and a transparent cap 2b attached to the distal end portion of the sheath body 2a. The sheath body 2a is formed of a rigid hollow member, such as a stainless-steel pipe, while the transparent cap 2b is formed of a transparent material, e.g., polycarbonate.

Figure 2:
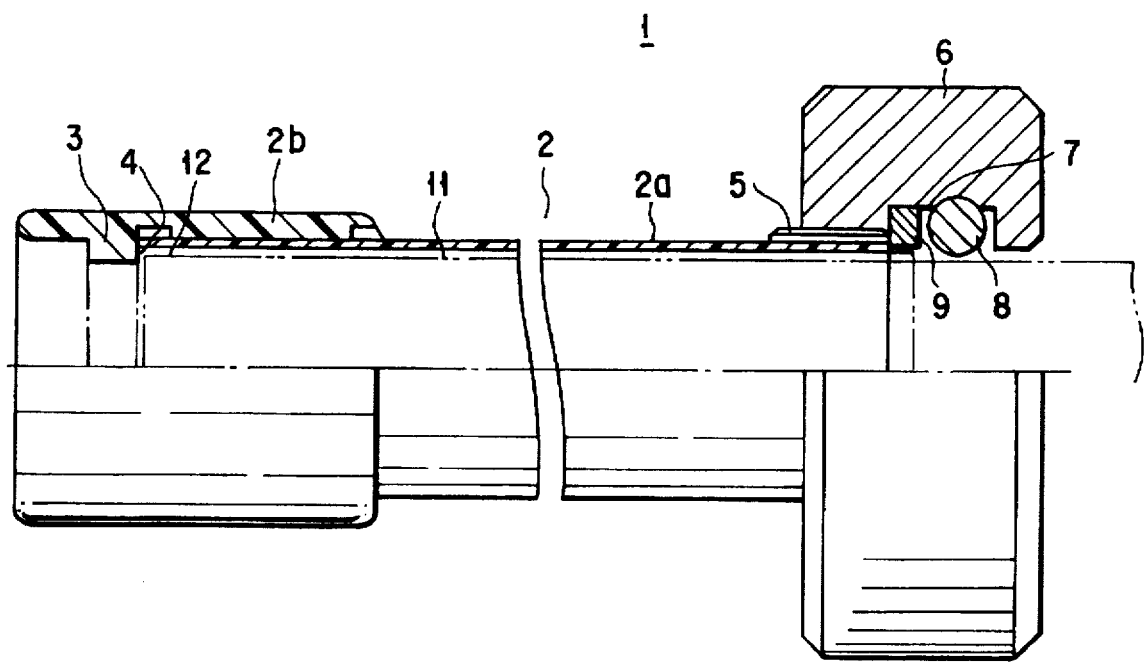
FIG. 2 is a longitudinal sectional view of the endoscopic sheath of FIG. 1.

As shown in FIG. 2, the transparent cap 2b has the shape of a hollow cylinder, and is formed integrally with a ring-shaped ridge 3 on the inner peripheral surface of the distal end portion thereof. The sheath body 2a is fixed to the ring-shaped ridge 3 by means of an adhesive agent or formed integrally therewith in a manner such that its distal end abuts against the side face of the ridge 3. The ring-shaped ridge 3 projects inward beyond the inner surface of the sheath body 2a, and the projecting inner surface of the ridge 3 serves as a stopper 4 which abuts against the distal end of an insert section 11 of a rigid endoscope 10 passed through the sheath body 2a, thereby preventing the distal end of the insert section 11 from projecting on the distal end side of the endoscope 10. The stopper 4 or the inner surface of the ring-shaped ridge 3 is situated in a position such that at least part of the distal end portion of the transparent cap 2b is within the view range of the rigid endoscope 10 with the distal end of its insert section 11 in contact with the stopper 4.

A screw section 5 is provided at the proximal end portion of the sheath body 2a. A grip 6 can be removably screwed on the screw section 5. An annular groove 7 is formed on the inner peripheral surface of the grip 6. An O-ring 8 and a backup ring 9 are housed in the groove 7.

When the grip 6 is screwed on the sheath body 2a with a distal end portion 12 of the insert section 11 of the rigid endoscope 10 held against the stopper 4 after the the insert section 11 is inserted into the sheath body 2a, the O-ring 8 is squeezed between the grip 6 and the backup ring 9 and projects inward. Thereupon, the insert section 11 of the rigid endoscope 10 is clamped by the O-ring 8 so that the sheath body 2a and the insert section 11 are fixed in a sealed state. Thus, the stopper 4, grip 6, and O-ring 8 constitute means for positioning the insert section 11 of the rigid endoscope 10 in the sheath section 2 so that at least part of the distal end portion (transparent cap 2b) of the sheath section 2 is within the view range of the endoscope 10.

FIG. 3 shows a monitor 13 to which the rigid endoscope 10 is connected. According to the present embodiment, as shown in FIG. 3, the whole circumference of the distal end edge of the transparent cap 2b is displayed on the monitor 13 for displaying an endoscopic image with the insert section 11 of the endoscope 10 inserted in the sheath body 2a so that the distal end portion 12 of the insert section 11 held against the stopper 4. Thus, the whole circumference of the distal end of the cap 2b is situated within the view range 14 of the endoscope 10.

Although the sheath body 2a and the transparent cap 2b, separate bodies, are fixed to each other according to the present embodiment, they may be formed integrally from the same material.

The following is a description of the way of carrying out herniation in an extraperitoneal approach by using the endoscopic sheath 1 and the rigid endoscope 10 constructed in this manner.

As shown in FIGS. 4 and 5, the navel region of the abdominal wall 15 is incised with a knife to leave the peritoneum 16 alone. An operator plunges his fingers into an incised region 17, and digitally detaches the peritoneum 16 downward from the abdominal wall 15.

Then, a trocar assembly 18 is inserted into the incised region 17, and the rigid endoscope 10 is guided into the patient's body through the bore of the assembly 18. In this case, the endoscopic sheath 1 is fitted on the insert section 11 of the endoscope 10, as shown in FIG. 2, and the transparent cap 2b of the sheath 1 and the distal end portion of the sheath body 2a is caused to project from the distal opening of the trocar 18. The rigid endoscope 10 is connected to a TV camera control unit 19 and a light source unit 20, and the trocar assembly 18 is connected to a gas feed and suction unit 21 so that a gas can be fed into the body cavity through the assembly 18.

In this state, a gas is fed from the gas feed and suction unit 21 into the body cavity through the trocar assembly 18 as the rigid endoscope 10, fitted with the endoscopic sheath 1, is oscillated from side to side or advanced to detach the peritoneum 16 dully from the abdominal wall 15 by means of the transparent cap 2b. As the operator detaches the peritoneum 16 in this manner, he observes and checks the detached region through the rigid endoscope 10 to see if there are no blood vessels or the like in the region.

The region cleared of the peritoneum 16 is inflated by the gas fed through the trocar assembly 18, whereby a space for a treatment is formed. Another trocar assembly inserted from another region of the abdominal wall 15 is introduced into this space, and an instrument is inserted into the space through this second trocar assembly. When the instrument is caused to approach a target region, a hernia sack is treated (ligated or excised) by means of the instrument under endoscopic observation. Thereafter, the hernia sack is covered with a mesh and sutured by means of a stapler or the like, as in the case of laparotomic herniation.

Retroperitoneal internal organs, such as the kidney, adrenal glands, etc., can be delivered after the rigid endoscope 10, fitted with the endoscopic sheath 1, is introduced into the patient's body from the back side and the skin and the posterior peritoneum are detached by means of the transparent cap 2b to secure a cavity.

Referring now to FIGS. 6 and 7, a method of causing the rigid endoscope 10, fitted with the endoscopic sheath 1 with the aforementioned construction, to approach the spine will be described.

FIG. 7 is a sectional view of a patient's body 250 taken along line 7—7 of FIG. 6. Located behind an abdominal wall 251, as shown in FIG. 7, is an abdominal cavity 252 which is surrounded by a peritoneum 253 and a posterior peritoneum 254, and a plurality of internal organs 256 exist in the abdominal cavity 252. Further, an intervertebral disk 257, articular processes 258, and a spinous process 259 exist behind the abdominal cavity 252 so as to be covered by the posterior peritoneum 254 and muscles 255. In order to cause the rigid endoscope 10, fitted with the endoscopic sheath 1, to approach the spine of the patient's body 250 constructed in this manner, the rear side wall is first incised by means of a knife. Then, the rigid endoscope 10 fitted with the endoscopic sheath 1 is guided into the patient's body through the incised region. In doing this, the posterior peritoneum 254 and the muscles 255 are detached by means of the transparent cap 2b as the endoscope 10 is caused to approach the intervertebral disk 257. Thereafter, a treatment, such as disk herniation, spinal fusion, or decompression of spinal cords, is conducted by means of an instrument (not shown) which is made to extend parallel to the endoscopic sheath 1.

Referring now to FIG. 8, the way appendectomy is carried out by using the rigid endoscope 10 fitted with the endoscopic sheath 1 constructed in the aforementioned manner will be described. As shown in FIG. 8, the navel region of the abdominal wall 15 is slightly incised with a knife, and the insert section 11 of the rigid endoscope 10 is inserted into a patient's body through the incised region 17. In this case, the endoscope 10 has a channel through which a forceps can be passed, and the endoscopic sheath 1 is fitted on its insert section 11.

In this state, air from the gas feed and suction unit 21 is fed into the abdominal cavity through a gas feed tube 22 and the channel of the rigid endoscope 10, whereupon the abdominal cavity is subjected to local pneumoperitoneum. Thus, a wide view range can be secured for the endoscope 10. Then, the vermiform appendix in the abdominal cavity is detected by means of the endoscope 10, and the basal part of the vermiform appendix is grasped by means of a grasp forceps (not shown) introduced into the abdominal cavity through the channel of the endoscope 10. In this state, the rigid endoscope 10 is removed from the incised region 17, and the vermiform appendix is pulled out of the abdominal cavity and excised. Thereafter, the residual tissue is sutured and returned to the abdominal cavity, and the incised region 17 is sutured. The grasp forceps may be introduced in parallel with the rigid endoscope 10 into the patient's body without being passed through the channel of the endoscope 10.

Figure 9:
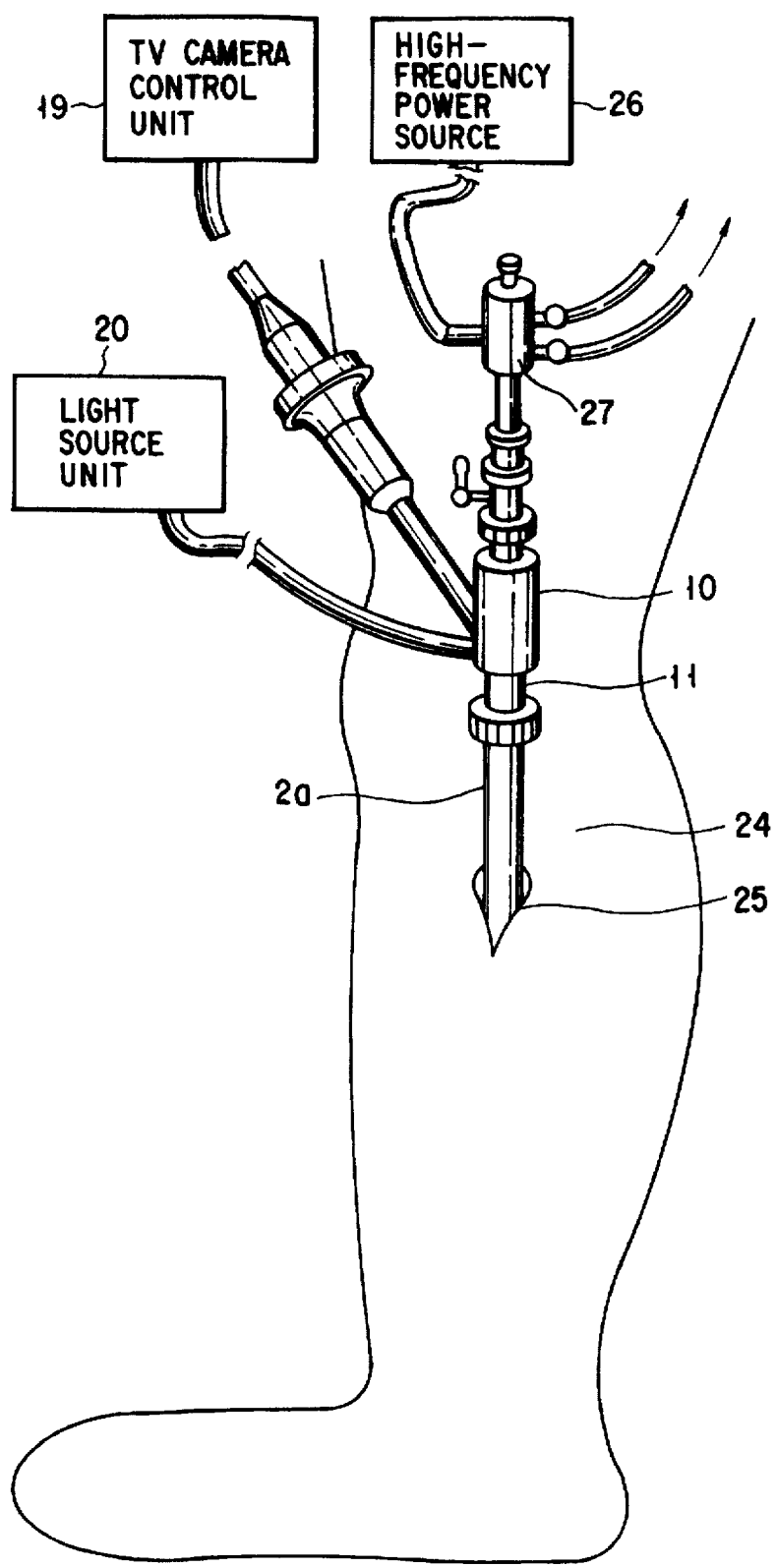
FIG. 9 is a view showing the way ramisection for an inferior limb is carried out by using the endoscopic sheath of FIG. 1.

Referring now to FIG. 9, the way ramisection is carried out for an inferior limb by using the rigid endoscope 10 fitted with the endoscopic sheath 1 constructed in the aforementioned manner will be described. As shown in FIG. 9, a central portion 24 of a crus is first slightly incised with a knife. Then, the fascia and muscles are detached digitally, the insert section 11 of the rigid endoscope 10 is inserted into an incised region 25, and rami communicantes are located. In this case, the endoscope 10 has the channel through which a forceps can be passed, and the endoscopic sheath 1 is fitted on the insert section 11.

When the position of the rami communicantes are located, a high-frequency electrode 27 connected to a high-frequency power source 26 is inserted into the channel of the rigid endoscope 10, and the rami communicantes are cauterized and blocked by means of the electrode 26. Thereafter, the incised region 25 is closed.

Besides the excision of these nerves, blood vessels of an inferior limb may be detached, excised, and taken out for vascular implantation. In doing this, small bifurcated blood vessels are blocked by clipping or cauterization.

Figure 10:
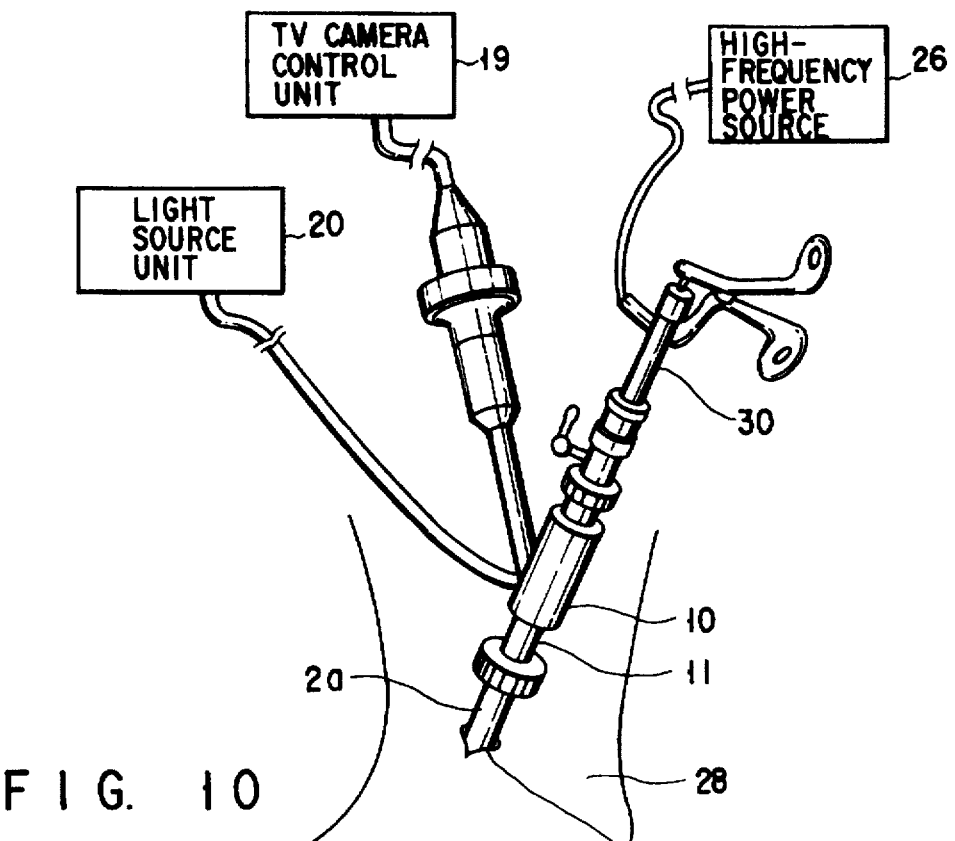
FIG. 10 is a view showing the way bolt extraction after the reduction of a fractured articulation of a foot is carried out by using the endoscopic sheath of FIG. 1.
Figure 11:
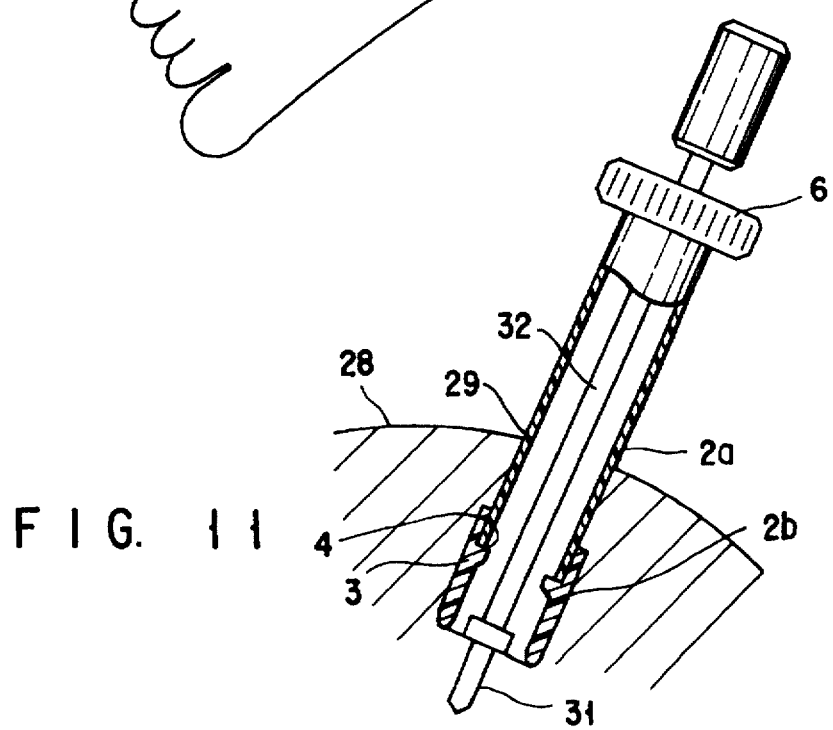
FIG. 11 is a sectional view showing a process of removing a bolt in the bolt extraction shown in FIG. 10.

Referring now to FIGS. 10 and 11, the way a bolt used in the reduction of a fractured articulation of a foot is removed by using the rigid endoscope 10 fitted with the endoscopic sheath 1 constructed in the aforementioned manner will be described. As shown in FIG. 10, a region near a foot articulation 28 is first slightly incised with a knife. Then, the insert section 11 of the endoscope 10 fitted with the endoscopic sheath 1 is inserted into an incised region 29, and a forceps 30 is inserted into the channel of the endoscope 10. The surrounding tissues are detached with the forceps 30 as the bolt is located by means of the endoscope 10.

When the bolt 31 is located, as shown in FIG. 11, the transparent cap 2b of the endoscopic sheath 1 is fitted on the head of the bolt 31, that is, the bolt head is caught in the cap 2b. In this state, the insert section 11 of the rigid endoscope 10 is removed from the sheath body 2a, and a screwdriver 32 is inserted into the body 2a instead. The bolt 31 is turned and removed from the mounting position by means of the screwdriver 32. Thereafter, the endoscopic sheath 1, along with the bolt 31, is removed from a patient's body, and the incised region 29 is closed.

Figure 12:
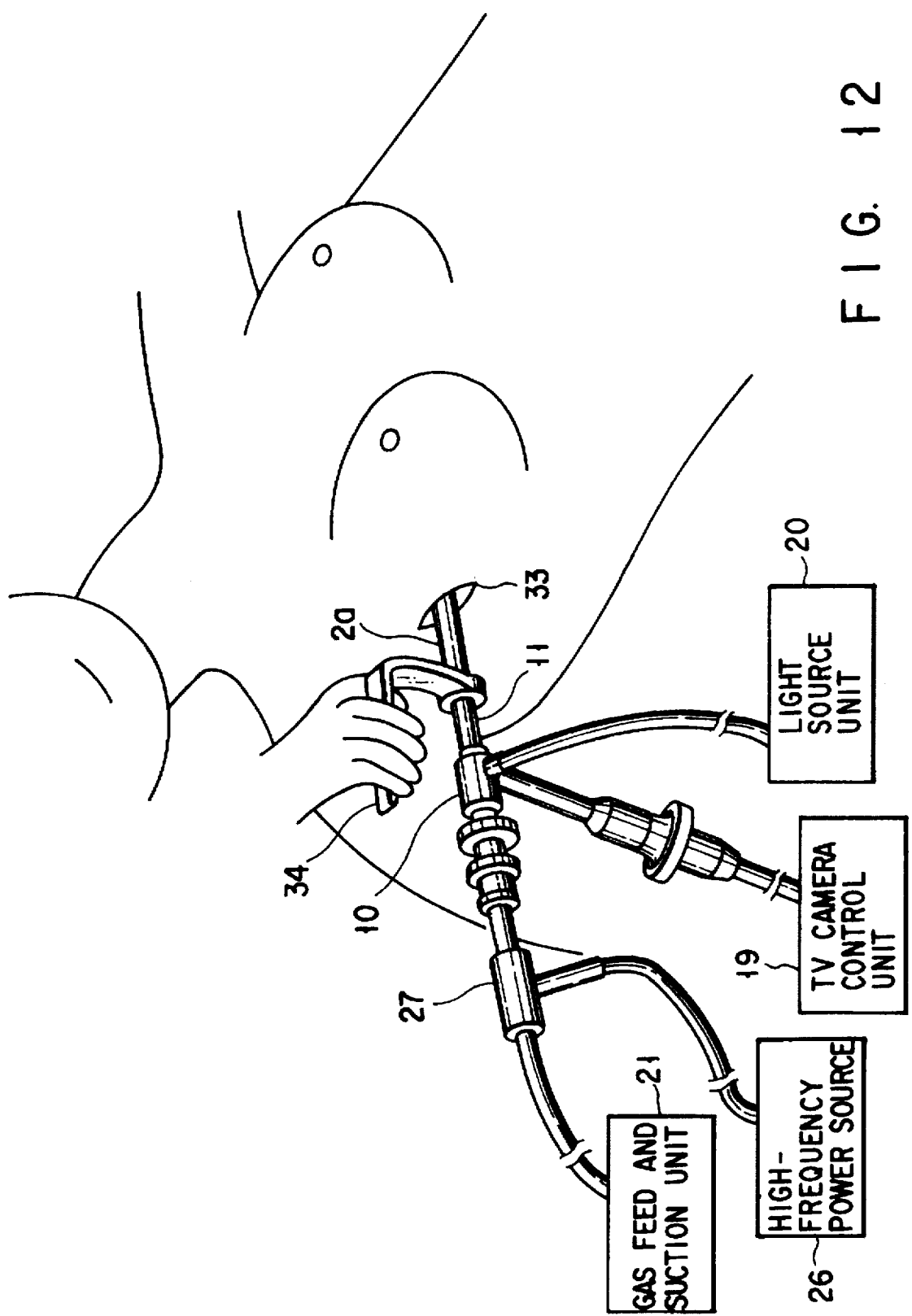
FIG. 12 is a view showing the way augmentation mammaplasty is carried out by using the endoscopic sheath of FIG. 1.

Referring now to FIG. 12, the way augmentation mammaplasty is carried out by using the rigid endoscope 10 fitted with the endoscopic sheath 1 constructed in the aforementioned manner will be described. First, a region under the armpit is slightly incised with a knife, as shown in FIG. 12. The insert section 11 of the endoscope 10 fitted with the endoscopic sheath 1 is inserted into a patient's body through an incised region 33, and its view range is secured. A handle 34 is provided on the proximal side of the sheath body 2a. Then, the high-frequency electrode 27 is introduced into the patient's body through the channel of the rigid endoscope 10, and detachment of tissue is advanced as the electrode 27 is used for incision and coagulation. Thereafter, an implant, such as a saline bag, is inserted into the pectoral region through the incised region 33, and a physiological saline is put into the bag to fill it out. When the incised region 33 is closed after leaving the impregnated saline bag in the pectoral region, the augmentation mammaplasty is completed.

With use of the endoscopic sheath 1 of the present embodiment, as described above, tissues and the like can be observed through the distal opening of the cylindrical transparent cap 2b, so that a subject region to be observed through the opening cannot be pressed by the sheath section 2. Thus, the states (color, shape, etc.) of living tissue can be observed and grasped accurately.

Conventionally, if no cavity is secured in a patient's body when only the rigid endoscope 10 is inserted into the patient's body, tissue may be caught and upset by a view window or the like of the insert section 11 of the endoscope 10, so that the treatment must inevitably be conducted substantially recklessly. According to the present embodiment, however, the rigid endoscope 10 is combined with the endoscopic sheath 1 which is composed of the sheath body 2a and the transparent cap 2b on the distal end portion thereof. Accordingly, there is no possibility of the transparent cap 2b entering the view range of the endoscope 10 so that the view window of the endoscope 10 is covered or narrowed by tissue. Thus, the view range can be secured at all times, so that the rigid endoscope 10 can be caused to approach the target region safely and securely.

According to the endoscopic sheath 1 of the present embodiment, moreover, at least part of the distal end portion of the transparent cap 2b enters the view range of the endoscope 10, so that the state of contact between the distal end portion of the cap 2b and living tissue can be recognized with ease. Thus, the sheath section 2, along with the endoscope 10, can be smoothly inserted into the patient's body without injuring it, so that the safety and reliability of the surgical operation can be improved.

According to the endoscopic sheath 1 of the present embodiment, furthermore, the cap 2b which enters the view range of the rigid endoscope 10 is formed from a transparent material in order to prevent the distal end portion of the cap 2b from interfering with the view range. Even when the distal end portion of the transparent cap 2b enters the view range of the endoscope 10, therefore, living tissue can be observed through the transparent portion.

If the endoscopic sheath 1 is inserted into subcutaneous tissue or any other organism which has no spaces therein, it pushes aside this tissue or organism, thereby positively creating a space in the region. If the endoscope 10 is passed through the sheath section 2 which is inserted in the subcutaneous tissue, for example, therefore, the subcutaneous tissue can be subjected to endoscopic observation through the transparent cap 2b or its distal opening.

As described in connection with the individual examples of surgical operations, the endoscopic sheath 1 according to the present embodiment has the following effects depending on the techniques.

[Herniation of FIG. 5]

(a) Since the peritoneum 16 or the like can be detached dully by means of the transparent cap 2b, manipulation is easy. In the case of hernia, in particular, the surroundings can be seen through the peritoneum 16 during the detachment of the peritoneum, the dull detachment by means of the transparent cap 2b can be carried out safely.

(b) Since gap between the insert section 11 of the transparent cap 2b and the sheath section 2 are sealed with the O-ring 8, the endoscopic sheath 1 can be used to perform gas feed into the patient's body or sucking operation.

[Reduction of Fracture of FIG. 11]

Since the treatment and operation can be carried out with the bolt 31 or some other member in the transparent cap 2b, there is no possibility of their damaging the surrounding tissues.

[Augmentation Mammaplasty of FIG. 12]

If the handle 34 is provided on the transparent cap 2b, the sheath section 2 can be easily moved back and forth, from side to side, and up and down, so that the treatment can be conducted smoothly.

FIG. 13 shows a second embodiment of the present invention. In the present embodiment, a tapered portion 42 is provided covering the whole circumference of the distal end portion of a transparent cap 2b. For other components, the second embodiment is constructed in the same manner as the first embodiment. According to this arrangement, the tapered portion 42 serves further to facilitate the detachment at the distal end of the transparent cap 2b.

FIG. 14 shows a third embodiment of the present invention. In the present embodiment, part of the distal end of a transparent cap 2b is cut aslant to form a slope 44. For other components, the third embodiment is constructed in the same manner as the first embodiment. According to this arrangement, the whole circumference of the distal end of the transparent cap 2b is covered by the view range of the endoscope 10, so that the state of contact between tissue and the distal end of the cap 2b can be recognized at all times, thus ensuring safety. In general, an endoscope has a deviation between its center and the center of its view range. If part of the distal end portion of the transparent cap 2b is cut aslant, as in the case of the present embodiment, interference with the view range can be minimized. If an instrument is introduced into a patient's body through the channel of the endoscope 10, in the arrangement of the present embodiment, safety can be ensured because the instrument can come into contact with tissue only in the view range of the endoscope 10.

Figure 16:
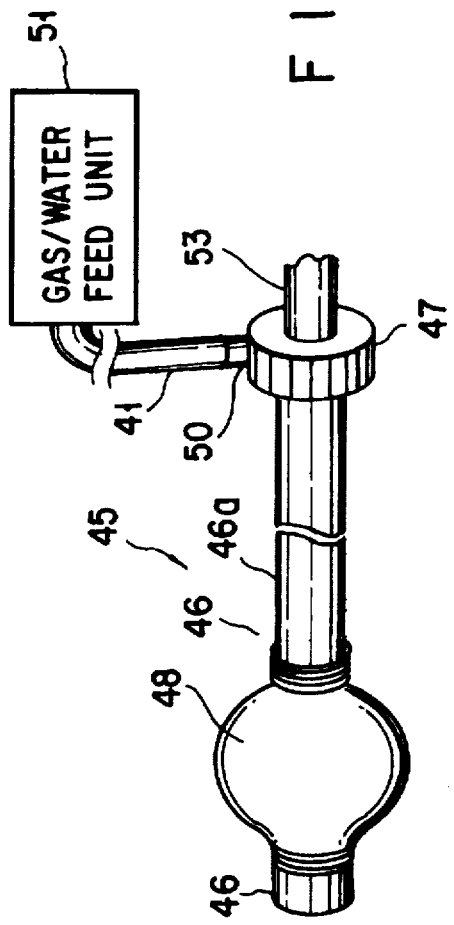
FIG. 16 is a perspective view showing an operating state of the endoscopic sheath of FIG. 15.

FIGS. 15 and 16 show a fourth embodiment of the present invention. As shown in FIG. 15, an endoscopic sheath 45 according to the present embodiment comprises a sheath section 46 which can be inserted into a patient's body. The sheath section 46 is composed of a tubular sheath body 46a and a cylindrical transparent cap 46b attached to the distal end portion of the sheath body 46a. A grip 47 is attached to the proximal end portion of the sheath body 46a. Also, a balloon 48 is fitted on the distal end portion of the sheath body 46a, adjoining the transparent cap 46b.

Both end portions of the balloon 48 are fastened to the sheath body 46a by means of strings. An adhesive agent is applied to the fastened portions so that the balloon 48 is fixed to the sheath body 46a. The side wall of the sheath body 46a is formed with an opening 49 which faces the balloon 48. The grip 47 is provided with a lure connector 50. The connector 50 is adapted to be connected with a tube 41 (see FIG. 16) which is connected to a gas/water feed unit 51. O-rings 54 and 55 are provided in grooves in the inner surfaces of the transparent cap 46b and the grip 47, respectively. When the endoscope 10 is inserted in the sheath section 46, the gap between the insert section 11 of the endoscope 10 and the sheath body 46a is sealed by the O-rings 54 and 55.

A ring-shaped ridge 3 is formed integrally on the inner peripheral surface of the distal end portion of the transparent cap 46b. The sheath body 46a is fixed to the ring-shaped ridge 3 by means of an adhesive agent or formed integrally therewith in a manner such that its distal end abuts against the side face of the ridge 3. The ring-shaped ridge 3 projects inward beyond the inner surface of the sheath body 46a, and the projecting inner surface of the ridge 3 serves as a stopper 4 which abuts against the distal end of the insert section 11 of the rigid endoscope 10 passed through the sheath body 46a, thereby preventing the distal end of the insert section 11 from projecting on the distal end side of the endoscope 10. The stopper 4 or the inner surface of the ring-shaped ridge 3 is situated in a position such that at least part of the distal end portion of the transparent cap 46b is within the view range of the rigid endoscope 10 with the distal end of its insert section 11 in contact with the stopper 4.

In the arrangement described above, if a gas or water is supplied from the gas/water feed unit 51 to the lure connector 50 through the tube 41, it can be fed into the balloon 48 through the gap between the insert section 11 of the endoscope 10 and the sheath body 46a, thereby inflating the balloon 48 (see FIG. 16). In carrying out the herniation shown in FIG. 5 from outside the peritoneum, for example, therefore, the abdominal wall 15 and the peritoneum 16 can be detached extensively at a stroke from each other by inflating the balloon 48 after being detached to some degree by means of the transparent cap 2b.

Thus, according to the endoscopic sheath 45 of the present embodiment, the same effects of the first embodiment can be produced naturally. Since the abdominal wall 15 and the peritoneum 16 can be detached extensively at a stroke from each other, moreover, manipulation is easy, and the operating time can be shortened. When the endoscopic sheath 45 is used in the abdominal cavity, furthermore, it can serve for the exclusion of surrounding tissues, thereby securing an operating field wide enough for smooth treatment.

Figure 17:
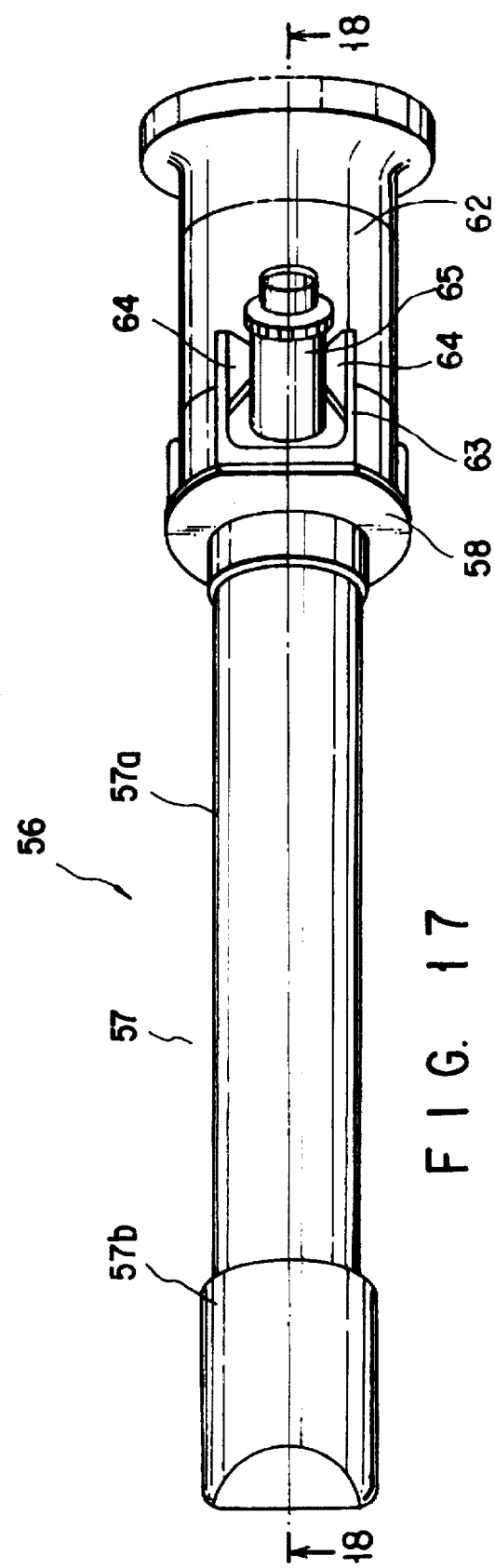
FIG. 17 is a perspective view of an endoscopic sheath according to a fifth embodiment of the invention.
Figures 18, 19:
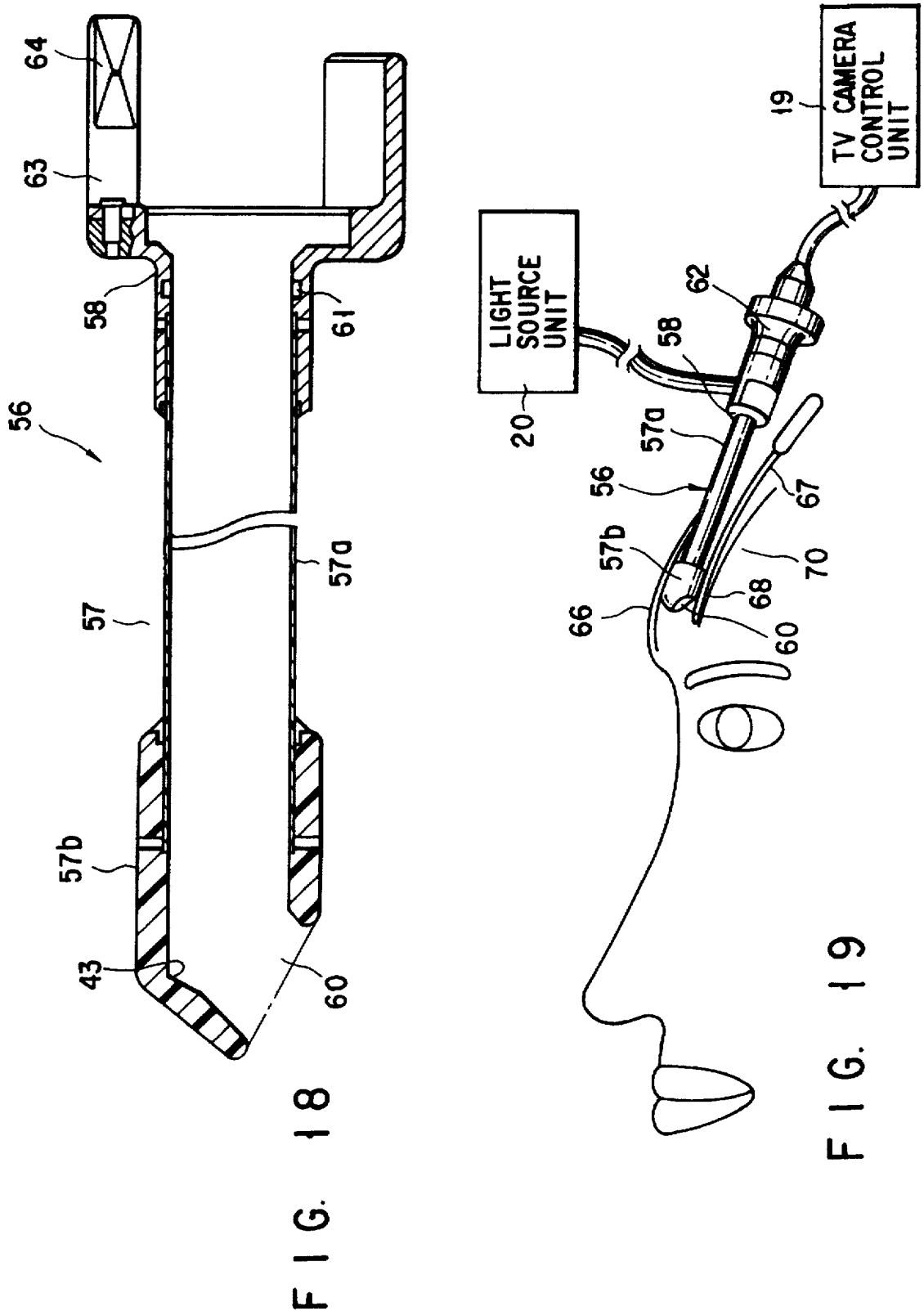
FIG. 18 is a longitudinal sectional view taken along line 18—18 of FIG. 17.
FIG. 19 is a view showing a technique for smoothing the forehead by using the endoscopic sheath of FIG. 17.

FIGS. 17 to 19 show a fifth embodiment of the present invention. As shown in FIG. 17, an endoscopic sheath 56 according to the present embodiment comprises a sheath section 57 which can be inserted into a patient's body. The sheath section 57 is composed of a tubular sheath body 57a and a substantially cylindrical transparent cap 57b attached to the distal end portion of the sheath body 57a. A substantially cylindrical receiving member 58 is attached to the proximal end portion of the sheath body 57a.

As shown in FIG. 18, the transparent cap 57b has a distal opening 60 which is slanted so as to fit the view range of a skew-vision rigid endoscope 62 which is adapted to be passed through the sheath section 57. The distal opening 60 is designed so that the view range of a direct-vision endoscope can be secured to some degree when it is passed through the sheath section 57. A sealing member 61 is provided in a groove which is formed in the inner surface of the receiving member 58. The sealing member 61 serves to maintain airtightness between the rigid endoscope 62 and the sheath body 57a.

As shown in FIGS. 17 and 18, the receiving member 58 is provided with a substantially U-shaped snap fit 63 which has springiness. A pair of conical projections 64 are arranged facing each other inside the snap fit 63. The distance between the projections 64 is a little shorter than the outside diameter of a light guide connector 65 of the rigid endoscope 62. Thus, when the endoscope 62 is inserted into the sheath body 57a, the connector 65 comes into contact with the projections 64. When the endoscope 62 is inserted deeper into the sheath body 57a, the snap fit 63 is widened so that the light guide connector 65 extends beyond the top of each projection 64. Thereupon, the snap fit 63 is restored to its initial position by its own urging force, whereby the rigid endoscope 62 is fixed to the sheath body 57a.

Formed on the inner peripheral surface of the distal end portion of the transparent cap 57b is an engaging portion 43 against which the skew-vision rigid endoscope 62 abuts. When the endoscope 62 is fixed to the sheath body 57a by the snap fit 63 so that the distal end of the insert section of the endoscope 62 abuts against the engaging portion 43, at least part of the open distal end portion of the transparent cap 57b is located within the view range of the endoscope 62.

Referring now to FIG. 19, a technique for smoothing the forehead by means of the endoscopic sheath 56 constructed in the aforesaid manner will be described.

First, a patient's scalp 66 near the forehead is incised with a knife. Then, the scalp 66 is dully detached from a cranial bone 70 by means of an instrument 67, such as a detachment forceps, as an incised region 68 is opened to a degree such that the endoscopic sheath 56 can be inserted therein. Thereafter, the rigid endoscope 62 fitted with the endoscopic sheath 56 is inserted into the incised region 68, while the scalp 66 is dully detached to the region near eyeballs with use of the instrument 67. Then, the skin of the forehead is elevated, the flabby skin is excised, and the remaining forehead skin and the scalp 66 are sewn up together. The direct-vision endoscope may be used in performing the aforementioned initial operation, while the skew-vision endoscope may be used in detaching hollow portions about the eyebrows.

According to the endoscopic sheath 56 of the present embodiment, as described above, the same effects of the first embodiment can be produced, and the rigid endoscope 62 can be fixed more easily and securely to the sheath body 57a, so that the treatment can be conducted smoothly with high operativity.

Figure 20:
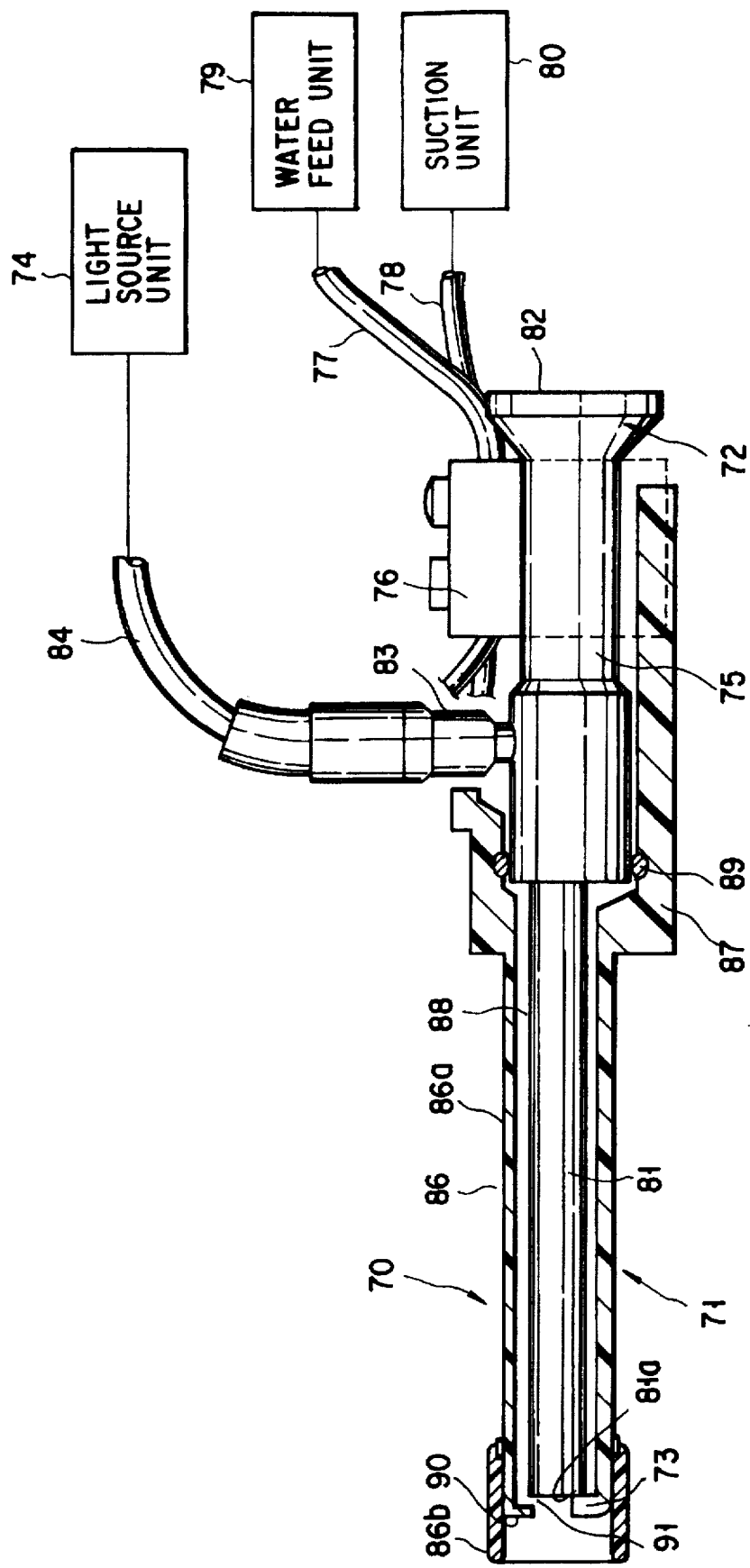
FIG. 20 is a longitudinal sectional view of an endoscopic sheath according to a sixth embodiment of the invention.

FIGS. 20 to 30 show a sixth embodiment of the present invention. According to the present embodiment, as shown in FIG. 20, an endoscopic apparatus 71 comprises a rigid endoscope 72, an endoscopic sheath 70 fitted on the endoscope 72, a light source unit 74 for supplying illumination light to the endoscope 72, a valve unit 76 removably mounted on a body section 75 of the endoscope 72 in a plurality of directions, and a water feed unit 79 and a suction unit 80 connected with a water feed tube 77 and a suction tube 78, respectively, which are connected to the valve unit 76.

The rigid endoscope 72 comprises a rigid insert section 81 formed of an elongate metallic pipe or the like, the thick body section 75 at the proximal end portion of the insert section 81, and an eyepiece section 84 at the proximal end of the body section 75. A light guide (not shown) for transmitting illumination light is passed through the insert section 81 of the endoscope 72. The proximal end of the light guide extends up to a light guide connector 83 on the body section 75. When the connector 83 is connected to the light source unit 74 by means of a light guide cable 84, the illumination light from the unit 74 is transmitted through the light guide cable 84 and the light guide in the endoscope 72, and is emitted forward from a distal emission face which is attached to an illumination window (not shown) on a distal end face 81a of the insert section 81. In this case, object light from a subject, such as an affected part, illuminated by the illumination light is focused on a focal plane by means of an objective lens (not shown) attached to a view window which is formed adjacent to the illumination window. The resulting optical image is delivered to the proximal end side by means of an image guide, such as a relay optical system (not shown), which is passed through the insert section 81 of the endoscope 72, and can be observed microscopically as an enlarged image through an eyepiece (not shown) at the eyepiece section 82.

The endoscopic sheath 70, which is removably fitted on the insert section 81 and the body section 75 of the endoscope 72, comprises a sheath section 86 and a grip 87 which are fitted on the insert section 81 and the body section 75, respectively, of the endoscope 72. The sheath section 86 is composed of a tubular sheath body 86a and a cylindrical transparent cap 86b formed on the distal end of the sheath body 86a. In this arrangement, the grip 87 is formed at the proximal end of the sheath body 86a. The transparent cap 86a is formed of a transparent material such as polycarbonate.

A line 88 is defined between the sheath body 86a and the insert section 81 of the endoscope 72. On the proximal side of the line 88, the gap between the grip 87 and the body section 75 of the endoscope 72 is sealed by means of an O-ring 89. A distal end 90 of the sheath body 86a is inwardly bent substantially at right angles, and in conjunction with the distal end face 81a of the endoscope 72, forms a nozzle 91 on the distal end side of the line 88.

The distal end portion of the sheath body 86a, which faces the nozzle 91, is inwardly bent substantially at right angles, and its inside faces serves as a stopper 73 which abuts against the distal end of the insert section 81 of the rigid endoscope 72 passed through the sheath body 86a, thereby preventing the distal end of the insert section 81 from projecting on the distal end side of the endoscope 72. When the distal end of the insert section 81 of the endoscope 72 is in contact with the stopper 73, at least part of the distal end portion of the transparent cap 86b is within the view range of the endoscope 72.

Figure 21:
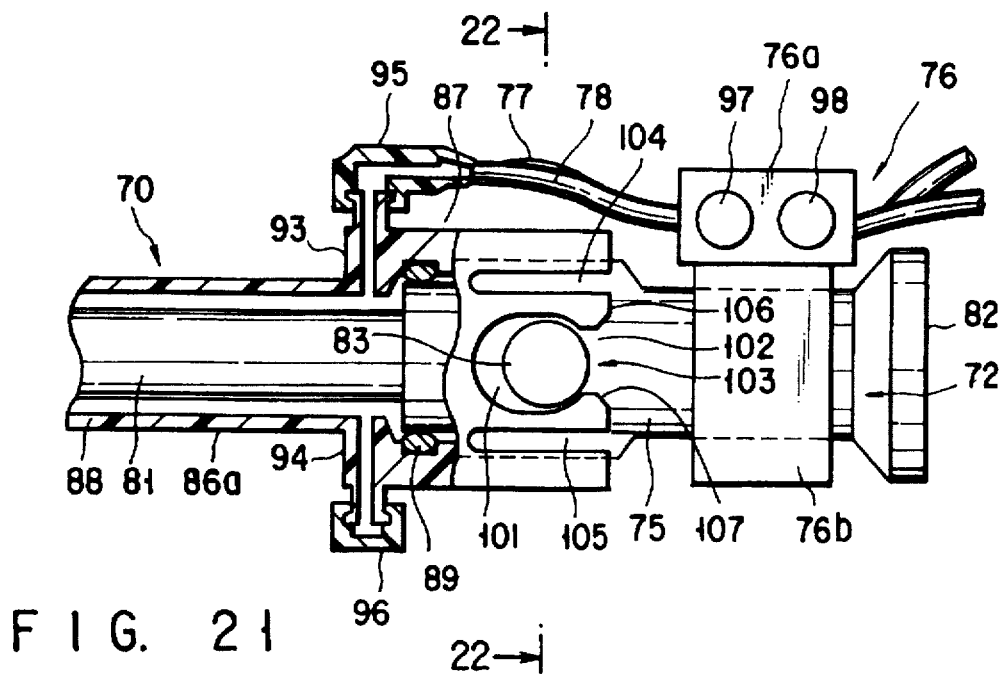
FIG. 21 is a side view of the proximal side of an endoscopic apparatus including the endoscopic sheath of FIG. 20.

As shown in FIG. 21, the proximal end side of the line 88 in the endoscopic sheath 70 internally connects with the respective bores of connectors 93 and 94 on the grip 87 on the distal end side of the O-ring 89. The connector 93 is removably connected with the water feed tube 77 and the suction tube 78 by means of a mounting portion 95 of the valve unit 76. Out of the connectors 93 and 94 on the grip 87, the connector 94 which is not connected with the mounting portion 95 is fitted with a cap 96 which closes the opening of the connector 94. By operating a water feed button 97 and a suction button 98 on the valve unit 76, as mentioned later, water feed and sucking operations for the tubes 77 and 78 can be started and stopped, and the flow rate of a liquid, such as water, flowing through the tubes 77 and 78 can be regulated.

Figure 22:
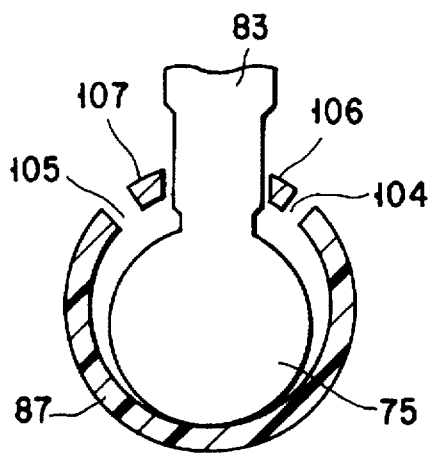
FIG. 22 is an enlarged sectional view taken along line 22—22 of FIG. 21.

As shown in FIGS. 21 and 22, the grip 87 is provided with a substantially U-shaped groove 103 and narrow grooves 104 and 105 arranged alternately, whereby two claws 106 and 107 are formed. The U-shaped groove 103 is composed of a wide portion 101, which has a width a little greater than the diameter of the light guide connector 83 of the rigid endoscope 72, and a narrow portion 102 at the open end, which has a width a little smaller than the diameter of the connector 83. When the insert section 81 of the endoscope 72 is inserted into the sheath body 86a, in this arrangement, the light guide connector 83 of the rigid endoscope 72 is held between the two claws 106 and 107. Thus, the endoscope 72 can be prevented from rotating or shifting in the longitudinal direction with respect to the endoscopic sheath 70.

Figures 23A, 23B:
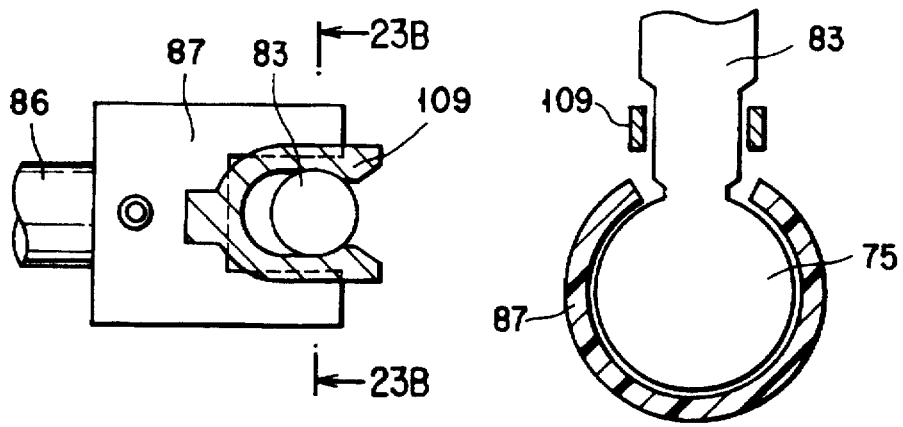
FIG. 23A is a plan view showing a modification of a proximal-side mounting structure of the endoscopic apparatus including the endoscopic sheath of FIG. 20.
FIG. 23B is an enlarged sectional view taken along 23B—23B of FIG. 23A.

Instead of forming the claws 106 and 107 on the grip 87 by means of the U-shaped groove 103 and the narrow grooves 104 and 105, a substantially U-shaped claw member 109 may be provided outside the grip 87, as shown in FIG. 23A or 23B.

Figure 26:
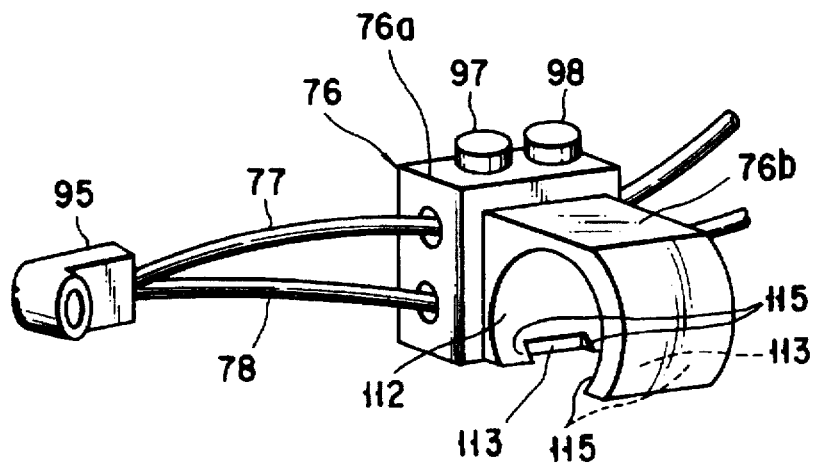
FIG. 26 is a perspective view of a valve unit of the endoscopic apparatus including the endoscopic sheath of FIG. 20.

The valve unit 76, which is removably mounted on the body section 75 of the endoscope 72 in a plurality of directions, is composed of a body portion 76a carrying the water feed button 97 and the suction button 98 thereon and a substantially U-shaped mounting portion 76b which is removably mounted on the body section 75 of the endoscope 72, as shown in FIG. 26.

Figure 24:
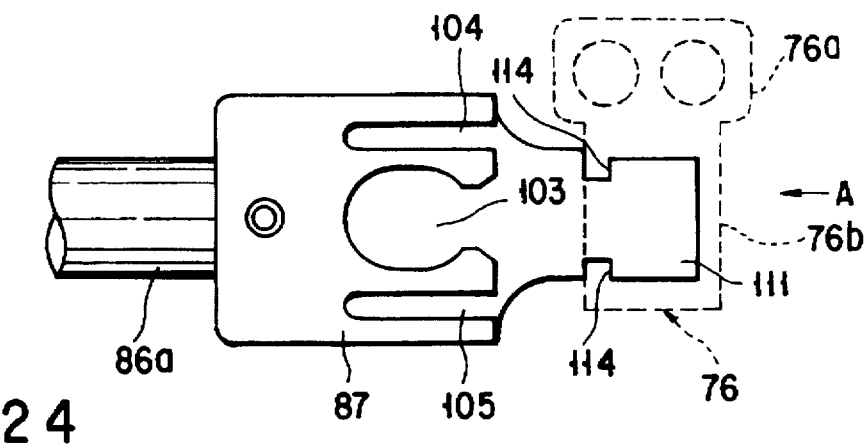
FIG. 24 is a plan view of a sheath body of the endoscopic sheath of FIG. 20.
Figure 25:
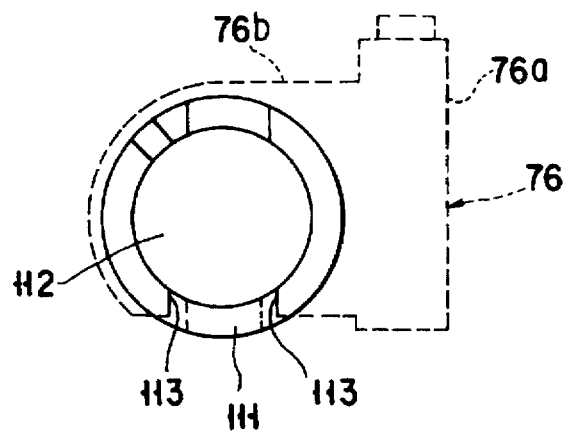
FIG. 25 is a fragmentary view taken in the direction of arrow A in FIG. 24.

When the valve unit 76 is mounted on the body section 75 of the rigid endoscope 72, it is fixedly positioned by the grip 87 of the endoscopic sheath 70. As shown in FIG. 24, a receiving portion 111 for receiving the valve unit 76 is provided at the lower part of the proximal end portion of the grip 8. The receiving portion 111 serves to settle the mounting position of the valve unit 76 and restrain the unit 76 from shifting its position. When the mounting portion 76b of the valve unit 76 is fitted on the body section 75 of the endoscope 72, both edges 113 of a mounting opening 112 of the valve unit 76 get engaged with the receiving portion 111, so that the unit 76 is restrained from rotating. In FIGS. 24 and 25, the valve unit 76 is illustrated by broken line and hatching to make its outline clear.

As shown in FIG. 24, the receiving portion 111 is provided with a pair of bisymmetrical groove portions 114. As shown in FIG. 26, moreover, a claw 115 is formed on each end of each edge 113 of the mounting portion 76b of the valve unit 76. When the valve unit 76 is mounted on the body section 75 of the rigid endoscope 72, according to this arrangement, two of the four claws 115 are fitted in their corresponding groove portions 114, whereby the unit 76 is restrained from moving in the axial direction with respect to the endoscope 72.

FIG. 27A is a bottom view of the endoscope 72 having its body section 75 fitted with the valve unit 76. FIG. 27B shows a state such that the valve unit 76 is mounted in a position opposite to the position shown in FIG. 27A. Since the valve unit 76 can be thus mounted on the endoscope 72 in a plurality of directions, the operator can select his desired mounting direction.

If the pair of groove portions 114 are arranged in a plurality of positions with respect to the longitudinal direction of the receiving portion 111, as shown in FIG. 27, for example, the valve unit 76 can be removably mounted any of these positions. Thus, the valve unit 76 can be mounted in any desired position and direction, so that the degree of freedom of selection of operativity can be improved.

Figure 28:
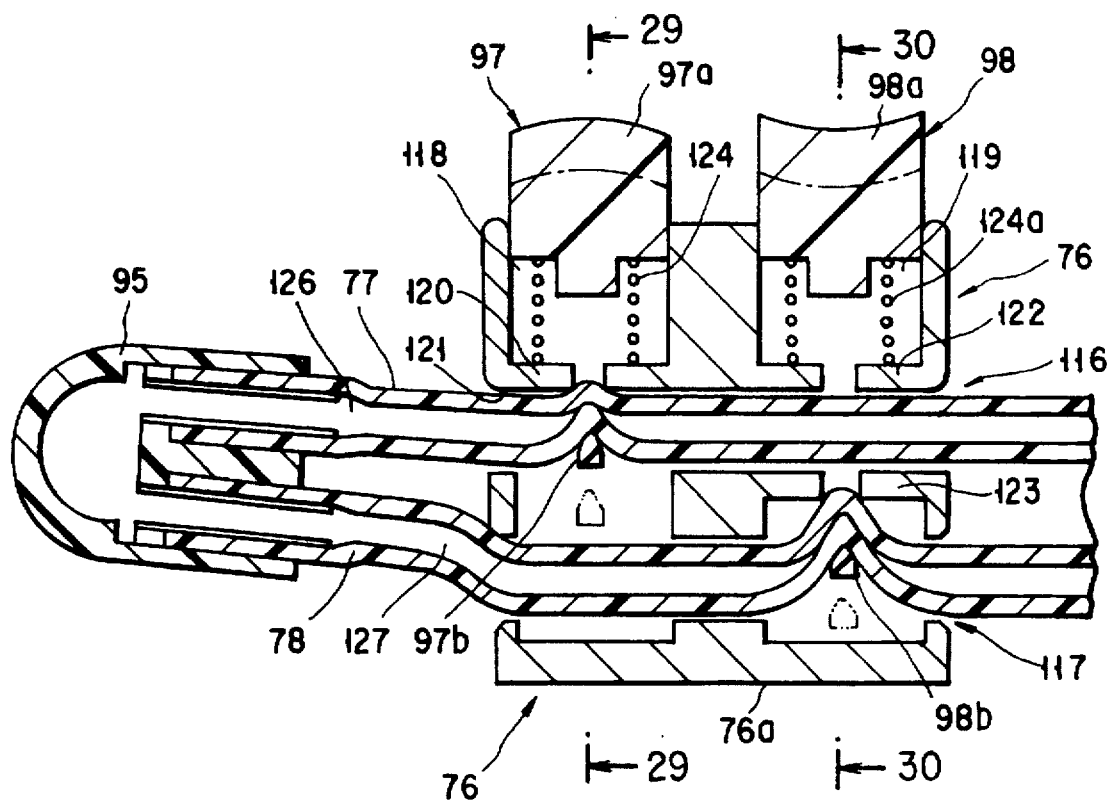
FIG. 28 is a sectional view of the valve unit of FIG. 26.

Referring now to FIGS. 28 to 30, the respective constructions of the body portion 76a of the valve unit 76 and the mounting portion 95 will be described.

As shown in FIG. 28, the valve body portion 76a has a water feed port 116 and a suction port 117. The ports 116 and 117 are arranged above and below so as to penetrate the body portion 76a horizontally. The water feed tube 77 and the suction tube 78 are passed through the water feed port 116 and the suction port 117, respectively.

Also, the valve body portion 76a is provided with first and second vertical holes 118 and 119 which cross the water feed tube 77 and the suction tube 78 so as to communicate vertically therewith and are arranged in front and in rear.

The water feed button 97 is fitted in the first vertical hole 118 for vertical movement. The button 97 is continually urged upward by a spring 124 which is supported on an inwardly protruding supporting portion 120 of the first vertical hole 118. As shown in FIG. 29, the water feed button 97 is composed of a button portion 97a and a frame-shaped backup portion 97b which extends downward from the button portion 97a and presses the water feed tube 77 continually against the supporting portion 120. The water feed tube 77 is passed through the frame of the backup portion 97b. In a normal state that the button portion 97a is not depressed, the tube 77 is pressed against the lower surface of the supporting portion 120 to be flattened by the hoisting action of the backup portion 97b caused by the urging force of the spring 124, so that a bore (line) 126 of the tube 77 is closed.

On the other hand, the suction button 98 is fitted in the second vertical hole 119 for vertical movement. The button 98 is continually urged upward by a spring 124 which is supported on an inwardly protruding supporting portion 122 of the second vertical hole 119. Further, a projecting portion 123 protrudes inward from that part of the second vertical hole 119 which is situated below the water feed port 116. As shown in FIG. 30, the suction button 98 is composed of a button portion 98a and a frame-shaped backup portion 98b which extends downward from the button portion 98a and presses the suction tube 78 continually against the projecting portion 123. The suction tube 78 is passed through the frame of the backup portion 98b. In a normal state that the button portion 98a is not depressed, the tube 78 is pressed against the lower surface of the projecting portion 123 to be flattened by the hoisting action of the backup portion 98b caused by the urging force of the spring 124, so that a bore (line) 127 of the tube 78 is closed. Although the water feed tube 77 is also passed through the frame of the backup portion 98b, in this case, its bore (line) 126 is not closed by the hoisting action of the backup portion 98b.

When the water feed button 97 is depressed against the urging force of the spring 124, in the arrangement described above, it moves to the position indicated by two-dot chain line in FIG. 29. Thereupon, the force to press the water feed tube 77 against the lower surface of the supporting portion 120 is lessened, so that tube 77 is restored to its original tubular shape by its own elasticity. As a result, the bore 126 of the water feed tube 77 opens, so that the liquid is allowed to be fed through the tube 77. The rate of liquid feed through the water feed tube 77 can be adjusted by changing the depth of depression of the water feed button 97.

When the suction button 98 is depressed against the urging force of the spring 124, on the other hand, it moves to the position indicated by two-dot chain line in FIG. 30. Thereupon, the force to press the suction tube 78 against the lower surface of the projecting portion 123 is lessened, so that tube 78 is restored to its original tubular shape by its own elasticity. As a result, the bore 127 of the suction tube 78 opens, so that the liquid is allowed to be fed through the tube 78. Also in this case, the rate of liquid feed through the suction tube 78 can be adjusted by changing the depth of depression of the suction button 98.

According to the endoscopic apparatus including the endoscopic sheath 70 of the present embodiment, as described above, the surface of the objective lens of the endoscope 72 can be cleaned by performing the water feed and sucking operations through a passage which includes the tubes 77 and 78, line 88, and nozzle 91, even in case the view range cannot be secured because the objective lens is soiled by blood or the like which is introduced into the transparent cap 86b during the surgical operation. If the objective lens is soiled, it is conventionally necessary to pull out the endoscope, along with the distal cap of the endoscopic sheath, from the patient's body, clean the objective lens of soil, and cause the endoscope to approach again to its original position (DE3743042A1, etc.). According to the arrangement of the present embodiment, however, the objective lens can be cleaned without removing the endoscope from the endoscopic sheath 70, so that the operating time can be shortened.

According to the present embodiment, moreover, the valve unit 76 can be removably mounted on the body section 75 of the endoscope 72, and its state (direction) of attachment can be selected freely (see FIGS. 27A and 27B). Accordingly, the operator can mount the valve unit 76 in his desired direction for ease of operation. In consequence, the endoscope can be held without effort during a surgical operation which requires subtle manipulations or many hours, and the buttons on the valve unit 76 can be operated with ease. Thus, the surgical operation can be advanced smoothly, and the operator's fatigue can be lightened.

Figure 31:
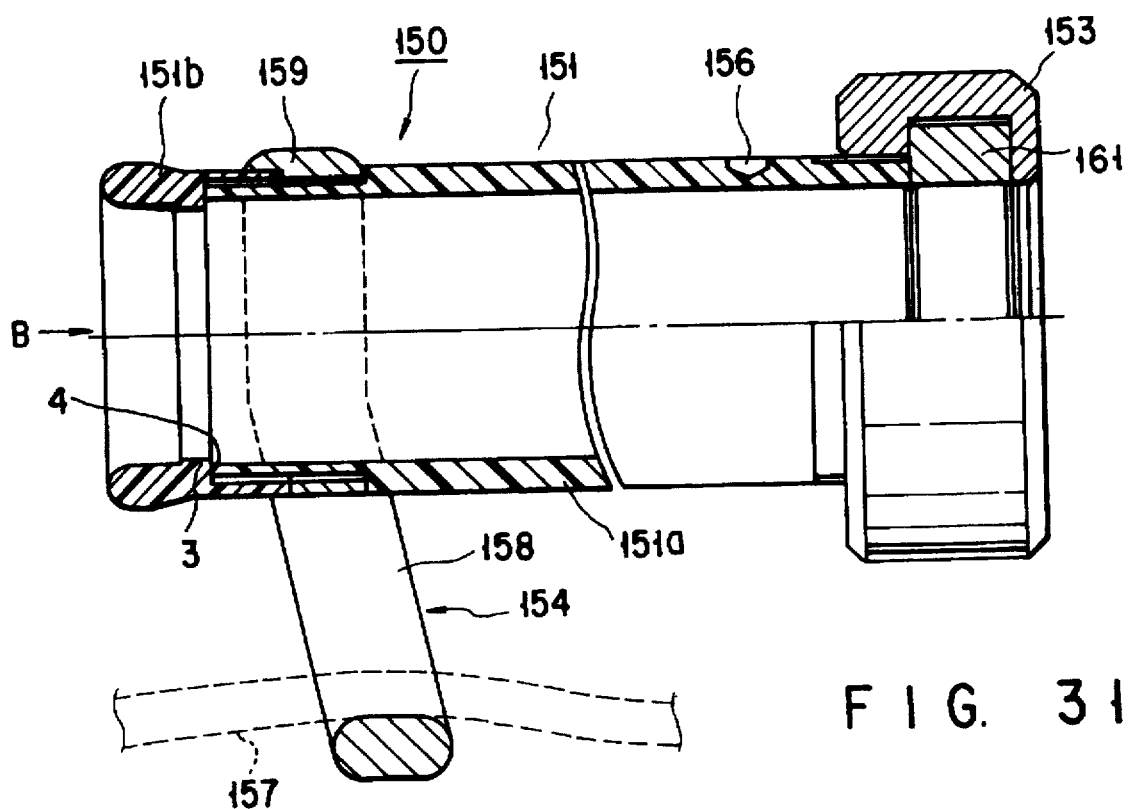
FIG. 31 is a longitudinal sectional view of an endoscopic sheath according to a seventh embodiment of the invention.
Figure 32:
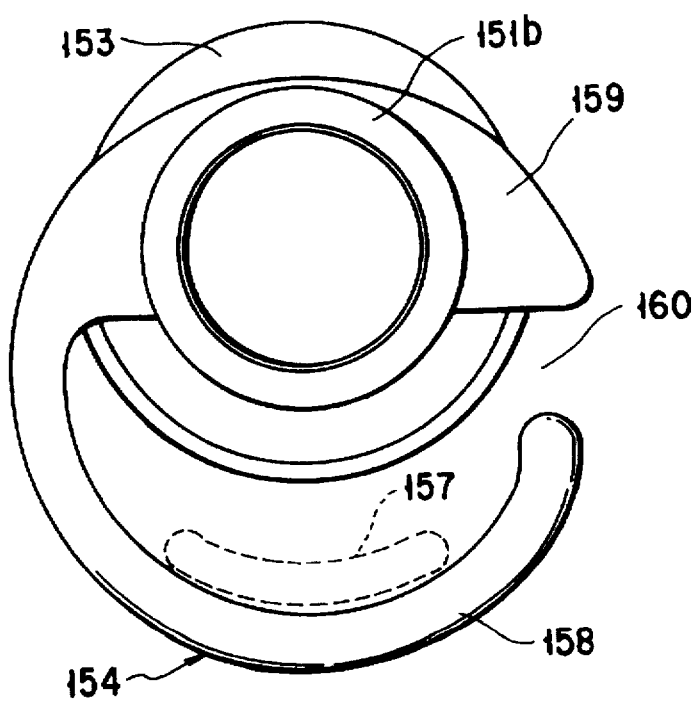
FIG. 32 is a fragmentary view taken in the direction of arrow B in FIG. 31.
Figure 33:
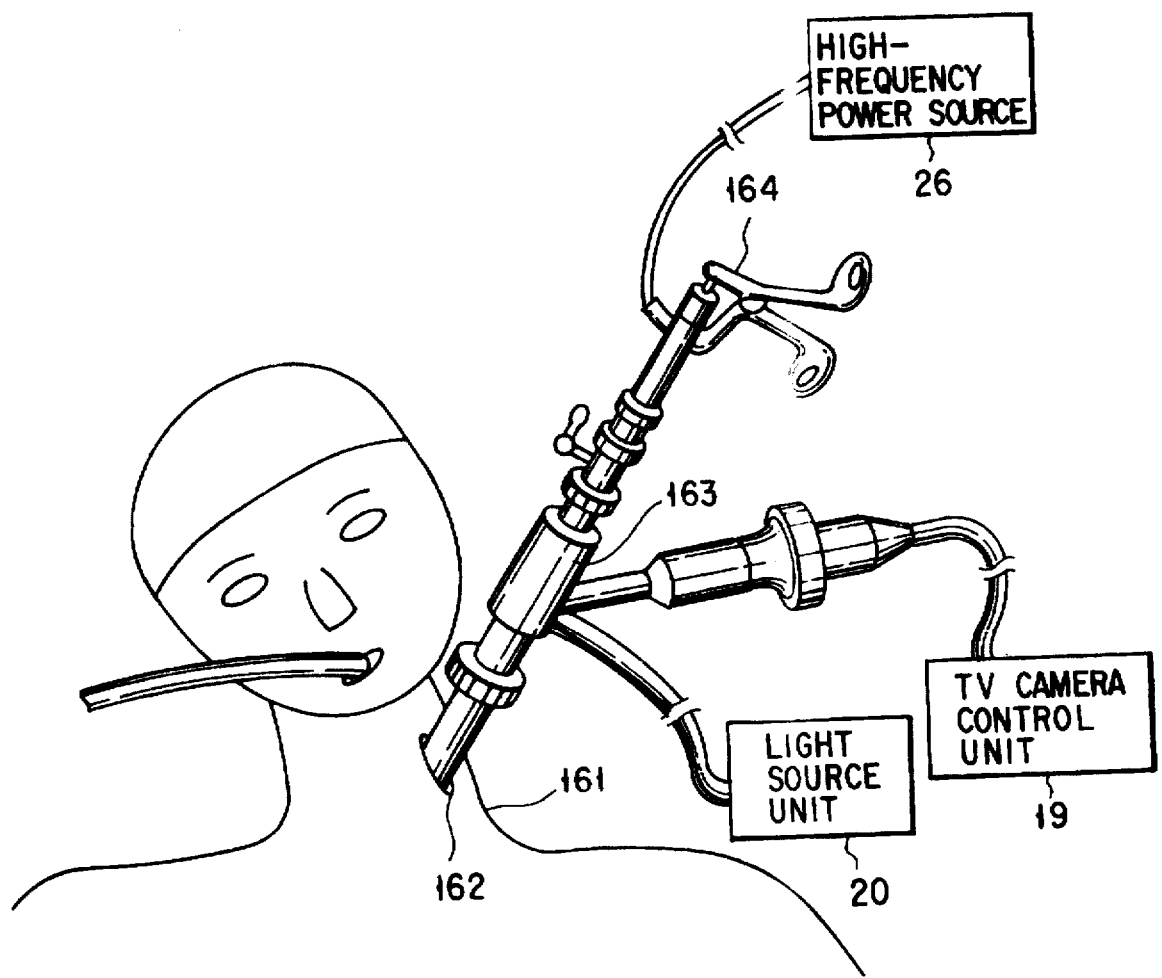
FIG. 33 is a view showing the way esophagectomy is carried out by using the endoscopic sheath of FIG. 31.

FIGS. 31 to 33 show a seventh embodiment of the present invention. As shown in FIGS. 31 and 32, an endoscopic sheath 150 according to the present embodiment comprises a sheath section 151 which can be inserted into a patient's body. The sheath section 151 is composed of a tubular sheath body 151a and a cylindrical transparent cap 151b attached to the distal end portion of the sheath body 151a. A grip 153 is attached to the proximal end portion of the sheath body 151a, and an arm 154 to the proximal end portion of the transparent cap 151b.

A ring-shaped ridge 3 protrudes integrally from the inner peripheral surface of the distal end portion of the transparent cap 151b. The sheath body 151a is fixed to the ring-shaped ridge 3 by means of an adhesive agent or formed integrally therewith in a manner such that its distal end abuts against the side face of the ridge 3. The ring-shaped ridge 3 projects inward beyond the inner surface of the sheath body 151a, and the projecting inner surface of the ridge 3 serves as a stopper 4 which abuts against the distal end of an insert section of an endoscope passed through the sheath body 151a, thereby preventing the distal end of the insert section from projecting on the distal end side of the endoscope. The stopper 4 or the inner surface of the ring-shaped ridge 3 is situated in a position such that at least part of the distal end portion of the transparent cap 151b is within the view range of the endoscope with the distal end of its insert section in contact with the stopper 4.

The arm 154 is composed of a mounting portion 159, which is fixedly connected to the transparent cap 151b and the sheath body 151a, and an arm body 158 in the form of a substantially semicircular loop declined to the proximal side with respect to the sheath body 151a. As shown in FIG. 31, the arm body 158 has a substantially elliptic cross section, and an opening 160 is provided between the arm body 158 and the mounting portion 159. The sheath body 151a has a marking 156 on its proximal side for indicating the direction in which the arm body 158 is situated. Thus, the operator can recognize the direction of the position of the arm body 158 on the proximal side.

The grip 153 is removably screwed on the sheath body 151a. An elastic member 161 of silicone rubber or the like is disposed in the bore of the grip 153. When the grip 153 is screwed onto the sheath body 151a, in this arrangement, the elastic member 161 is squeezed so that the gap between the endoscopic sheath 150 and the endoscope (not shown) inserted therein is sealed. The state of sealing between the endoscopic sheath 150 and the endoscope can be changed by adjusting the depth of engagement of the grip 153.

Referring now to FIG. 33, the way the endoscopic sheath 150 with the aforementioned construction is used for esophageal ablation in esophagectomy.

First, a patient's cervical part 161 is incised with a knife, as shown in FIG. 33. After an esophageal portion 157 around an incised region 162 is digitally detached, an endoscope 163 with the endoscopic sheath 150 fitted thereon is inserted into the incised region 162. At this time, the detached esophageal portion 157 is put into the loop of the arm body 158 through the opening 160 of the arm 154. With the esophageal portion 157 caught by the arm body 158, restiform bodies or blood vessels are excised or clipped by means of a forceps 164 (or electrode or clip) introduced into the patient's body through a channel of the endoscope 163 to advance detachment. Thus, the arm body 158 always catches the detached esophageal portion 157.

While one operator is carrying out the above surgical operation, another operator prepares a stomach tube to serve as an substitute for the esophagus after the esophagectomy, and digitally detaches the lower part of the esophageal portion 157 in a direct-vision manner. When the detachment, excision, and evulsion of the esophageal portion 157 are finished, the incised region 162 is closed by anastomosing the stomach tube and the excised end of the cervical part 161.

According to the endoscopic sheath 150 of the present embodiment, as described above, the same effects of the first embodiment can be produced naturally, and the detachment of the esophagus, which has conventionally been able to be carried out only blindly and digitally, can be conducted under the observation through the endoscope, thus ensuring a safe reliable surgical operation.

Since the endoscopic sheath 150 can be introduced into the patient's body in a manner such that the arm 154 is always guided along the esophageal portion 157, the region around the esophageal portion 157 can be approached without missing the esophageal portion 157, so that the esophagus can be detached with ease. Thus, the surgical operation can be carried out safely and securely.

Since the arm body 158 of the endoscopic sheath 150 is declined to the proximal side, moreover, only the detached esophageal portion 157 is caught by the arm body 158. In other words, only the detached esophageal portion 157 can enter the loop of the arm body 158. Thus, the esophageal portion 157 or its surrounding tissues cannot be carelessly damaged outside the view range.

Figure 34:
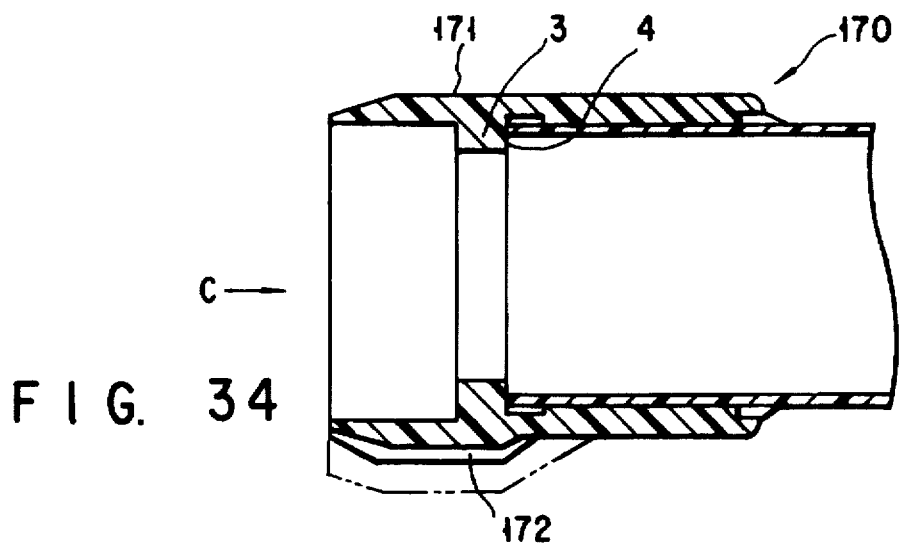
FIG. 34 is a longitudinal sectional view of an endoscopic sheath according to an eighth embodiment of the invention.
Figure 35:
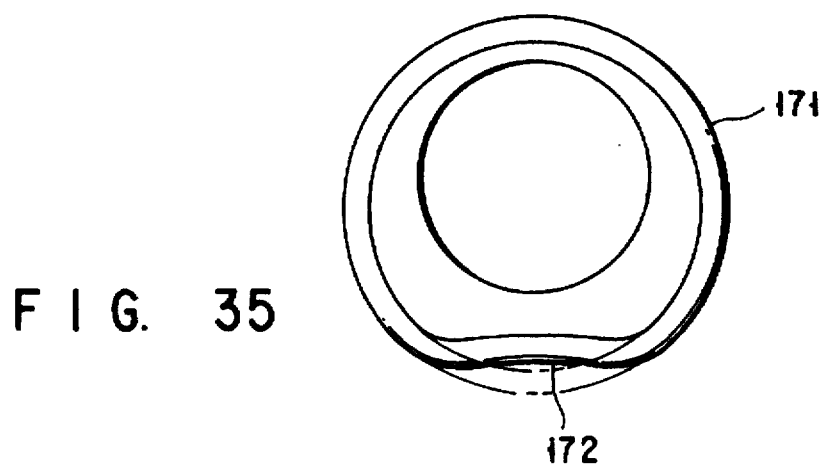
FIG. 35 is a fragmentary view taken in the direction of arrow C in FIG. 34.

FIGS. 34 and 35 show an eighth embodiment of the present invention. In an endoscopic sheath 170 according to the present embodiment, a smooth recessed portion 172 is formed extending in the axial direction in the outer surface of a transparent cap 171. For other components, the eighth embodiment is constructed in the same manner as the seventh embodiment.

When using the endoscopic sheath 170 for the detachment of the esophageal portion 157 in esophagectomy, the sheath 170 is inserted through the incised region 162 (see FIG. 33) with the recessed portion 172 extending along the esophageal portion 157. Then, restiform bodies or blood vessels are treated with a forceps (or clip or other instrument), which is inserted in the patient's body in parallel with the sheath 170, as the esophageal portion 157 is detached by means of the distal end portion of the transparent cap 171.

Thus, the endoscopic sheath 170 of the present embodiment can be guided along the esophageal portion 157 by the recessed portion 172 of the transparent cap 171 as it approaches the region around the esophageal portion 157, so that the esophageal portion 157 can be detached safely and securely.

Figure 36:
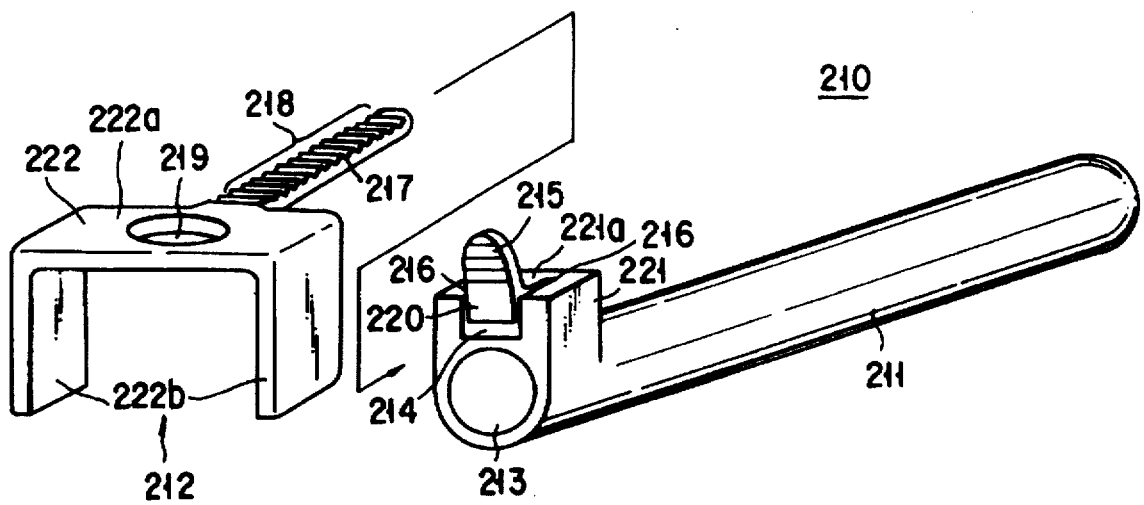
FIG. 36 is a perspective view of an endoscopic sheath according to a ninth embodiment of the invention.

FIGS. 36 to 41 show a ninth embodiment of the present invention. As shown in FIG. 36, an endoscopic sheath 210 according to the present embodiment comprises a tubular sheath section 211, having a bore 213 through which an insert section 225 (see FIG. 37) of an endoscope 224 can be passed, and a positioning member 212 for positioning the endoscope 224 with respect to the sheath section 211.

The sheath section 211 is formed substantially entirely of a transparent plastic material, such as polycarbonate or polystyrene. A projecting portion 221 is provided on the proximal side of the transparent sheath section 221. A through hole with a rectangular cross section is bored through the projecting portion 221 in the axial direction thereof. Formed in the upper surface of the projecting portion 221 are two slits 216 which communicate with the through hole 214. The slits 216 extend parallel to each other along the through hole 214 from one end of the projecting portion 221, and terminates in the vicinity of the other end of the projecting portion 221. Accordingly, an upper surface region 221a of the projecting portion 221, which is sandwiched between the two slits 216, can be deformed like a cantilever. The upper surface region 221a is formed integrally with a lug 220 which projects into the through hole 214 and is adapted to engage the positioning member 212. Also, the upper surface region 221a is formed integrally with a push member 215 which extends in the direction opposite to the lug 220, that is, upward. When the push member 215 is pushed toward the distal end, in this arrangement, the lug 220 is lifted up.

The positioning member 212 includes a substantially U-shaped plate portion 222 which is composed of a top plate 222a, having an aperture 219 in the center through which a light guide adapter 226 (see FIG. 37) of the endoscope 224 can be passed, and a pair of side plates 222b which extend vertically downward from the opposite sides of the top plate 222a. The side plates 222b are adapted to be fitted on a flange portion 227 (see FIG. 37) of the endoscope 224, thereby connecting the positioning member 212 and the endoscope 224.

An elongate engaging plate 217 extends horizontally from the top plate 222a. The plate 217 extends substantially from the plate portion 222, and its upper surface is flush with that of the plate 222a. The engaging plate 217 has a width and a thickness such that it can be inserted into the through hole 214 of the projecting portion 221. The upper surface of the engaging plate 217 is formed with a plurality of grooves 218 which, arranged in the longitudinal direction of the plate 217, are adapted to engage the lug 220 of the projecting portion 221.

The following is a description of the case where the endoscopic sheath 210 with the above construction is used in combination with the endoscope 224.

First, the positioning member 212 is attached to the endoscope 224 by fitting the light guide adapter 226 of the endoscope 224 into the aperture 219 of the positioning member 212 and fitting the side plates 222b onto the flange portion 227 of the endoscope 224, as shown in FIG. 37. At this time, the engaging plate 217 is directed to the distal end of the endoscope 224. In this state, the insert section 225 of the endoscope 224 is inserted into the transparent sheath section 211, and the engaging plate 217 is passed through the through hole 214 of the projecting portion 221. In this case, the distal end of the endoscope 224 is positioned in the sheath section 211 by the positioning member 212 so that at least part of the distal end portion of the sheath section 211 is within the view range of the endoscope 224, as shown in FIG. 37. In doing this, the operator moves the positioning member 212 to change the position of engagement between the grooves 218 of the engaging plate 217 and the lug 220 of the projecting portion 221 while watching a monitor 228 (see FIGS. 38 and 39) which displays an endoscope image. The lug 220 can be disengaged from the grooves 218 by pressing the push member 215 to the distal end side to deform the upper surface region 221a of the projecting portion 221, as shown in FIG. 41. Thus, the engaging plate 217 can be freely moved in the through hole 214 of the projecting portion 221, and the position of the distal end of the endoscope 224 can be changed with ease. FIG. 38 shows a display screen of the monitor 228 which displays the distal end of the transparent sheath section 211 in the view range of the endoscope 224. If the sheath section 211 is unnecessary, the distal end of the endoscope 224 should only be caused to project from the distal opening of the sheath 211, as shown in FIG. 40. In this case, the transparent sheath section 211 is not within the view range of the endoscope 224, so that it is not displayed on the display screen of the monitor 228, as shown in FIG. 39. Naturally, the endoscope 224 is fixed to the sheath section 211 as the grooves 218 of the engaging plate 217 are in engagement with the lug 220 of the projecting portion 221.

As described above, the endoscopic sheath 210 of the present embodiment can produce the same effects of the first embodiment, and besides, its operativity is satisfactory since the distal end of the endoscope 224 can be held in a desired position with respect to the transparent sheath section 211. Since the endoscopic sheath 210 is formed of a single transparent material without a cap, moreover, it can be manufactured at low cost.

Figure 42:
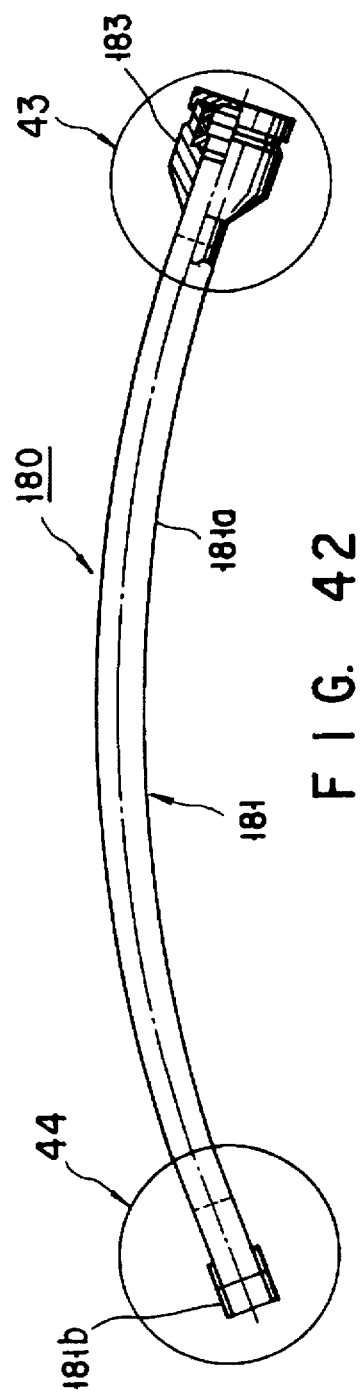
FIG. 42 is a side view, partially in section, showing a bendable endoscopic sheath.
Figure 44:
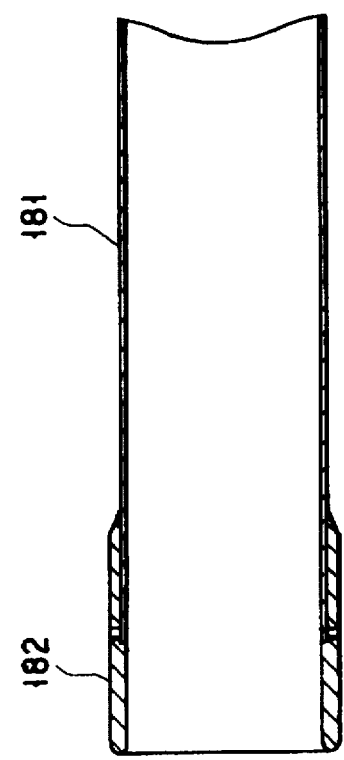
FIG. 44 is an enlarged half-sectional view showing a section 44 shown in FIG. 42.
Figure 43:
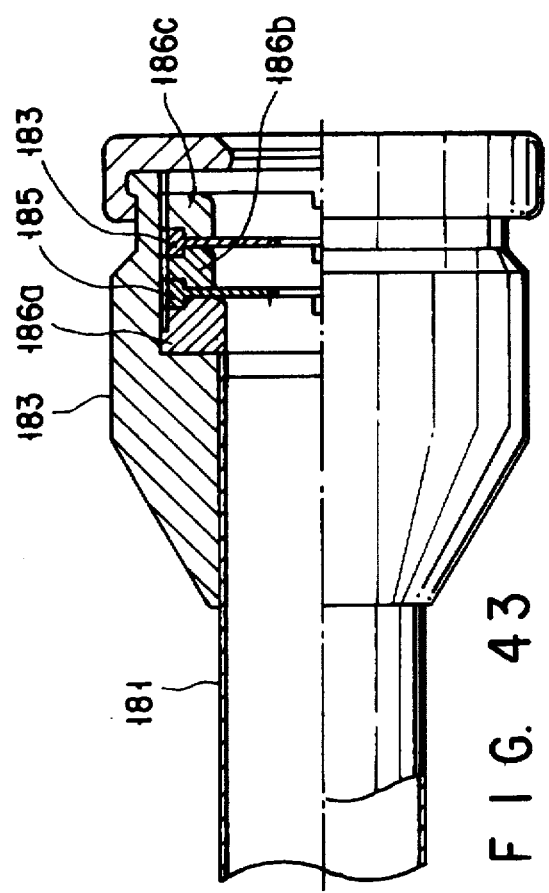
FIG. 43 is an enlarged half-sectional view showing a section 43 shown in FIG. 42.

FIGS. 42 to 44 show an endoscopic sheath with an alternative configuration. An endoscopic sheath 180 shown in FIG. 42 comprises a sheath section 181 which can be inserted into a patient's body. The sheath section 181 is composed of a tubular sheath body 181a and a cylindrical transparent cap 181b, which is formed of a transparent material, such as polycarbonate, and is fixed to the distal end portion of the sheath body 181a (see FIG. 44). A cylindrical grip 183 is attached to the proximal end portion of the sheath body 181a.

As shown in FIG. 43, two rubber valves 185 are pressed and fixed in the bore of the grip 183 by means of backup plates 186a, 186b and 186c. Thus, the airtightness of an endoscope passed through the endoscopic sheath 180 can be maintained. The sheath body 181a has a curl with a predetermined radius of curvature along the curvature of the patient's esophageal portion 157.

In detaching the esophagus by using a combination of the endoscopic sheath 180 with the aforementioned construction and a flexible endoscope (not shown), a flexible instrument is introduced into a patient's body through a treatment channel of the flexible endoscope, and the esophagus is detached by means of the flexible instrument. In doing this, the flexible endoscope may be kept projecting from the distal end of the endoscopic sheath 180.

In the endoscopic sheath 180 described above, the sheath body 181a is curved along the curvature of the esophageal portion 157, so that the esophagus can be detached more smoothly. Since the flexible endoscope can take any desired position in this endoscopic sheath 180, moreover, the degree of freedom of operation can be improved.

Figure 45:
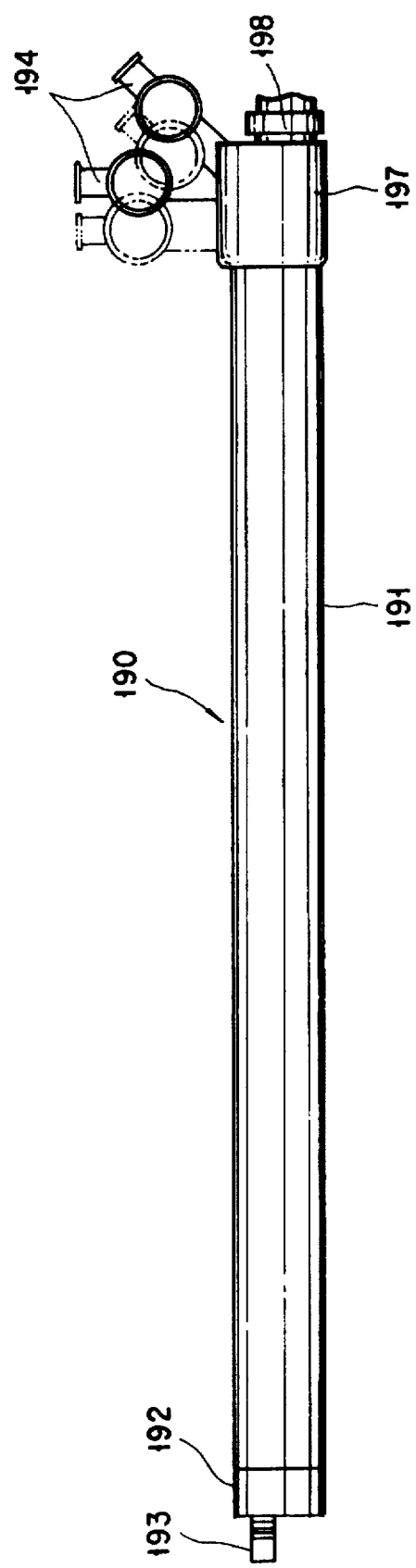
FIG. 45 is a side view of an endoscopic sheath having a treatment channel and an endoscopic channel.
Figure 46:
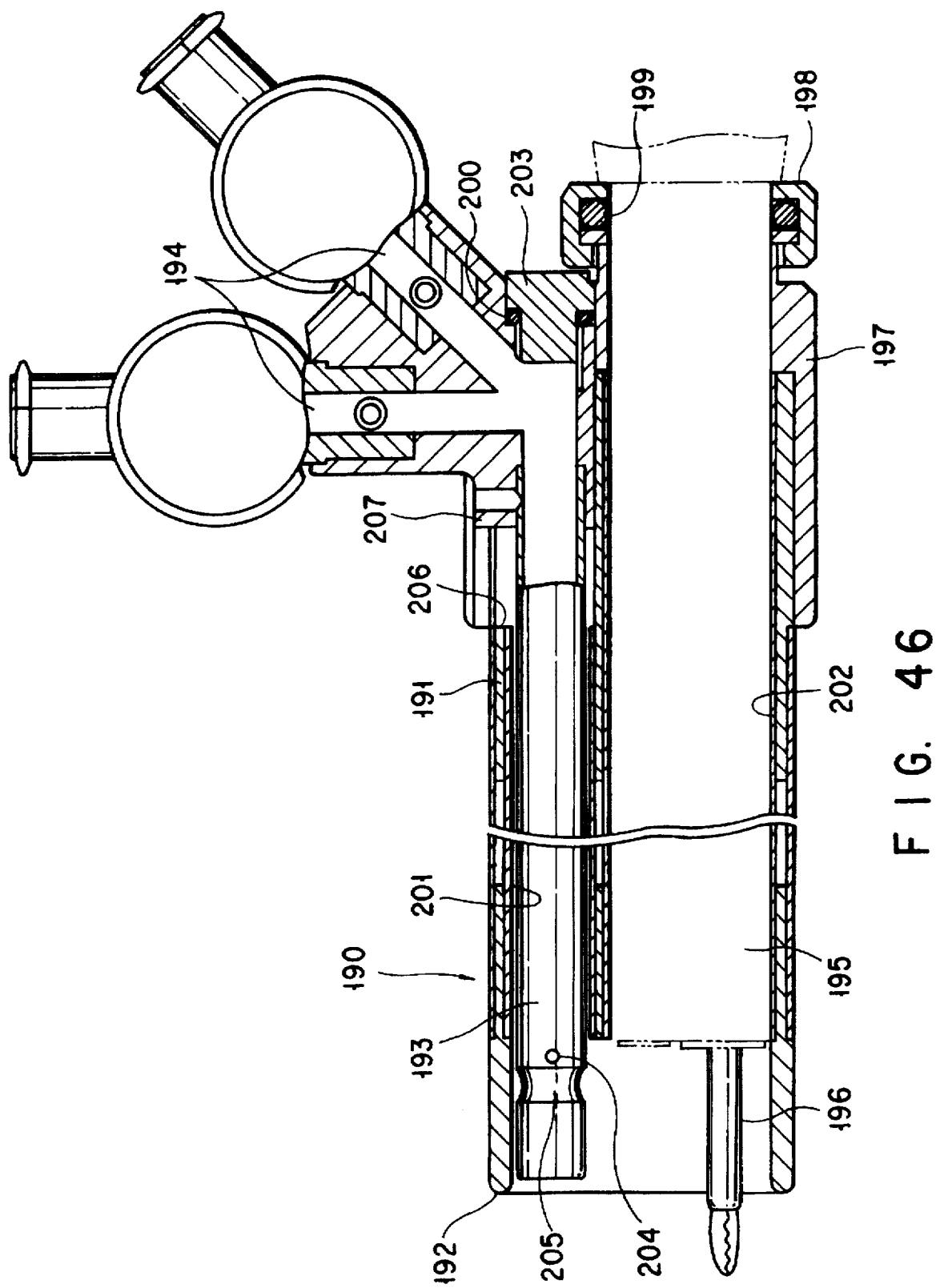
FIG. 46 is a longitudinal sectional view of the endoscopic sheath of FIG. 45.

An endoscopic sheath 190 shown in FIGS. 45 and 46 comprises a sheath body 191, a transparent cap 192 formed of a transparent material, such as polycarbonate, acrylic resin, polystyrene, or zeonex, and fixed to the distal end portion of the sheath body 191, and a fixing member 197 at the proximal end portion of the sheath body 191.

As shown in FIG. 46, the endoscopic sheath 190 is provided with a treatment lumen 201 and an endoscopic lumen 202 which extend parallel to each other along the sheath body 191 and the fixing member 197. The lumina 201 and 202 join together into one lumen in the bore of the transparent cap 192. A water feed and suction pipe 193 is slidably inserted in and connected to the treatment lumen 201 from the distal end side thereof. Inserted in the endoscopic lumen 202 is an endoscope 195 through which an instrument 196 can be passed. The treatment lumen 201 may be formed at an angle to the endoscopic lumen 202. In this case, the water feed and suction pipe 193 can be introduced securely and quickly into the view range of the endoscope 195.

The fixing member 197 is provided with two water feed and suction channels 194 which, inclined at an angle to each other, communicate with the proximal end portion of the treatment lumen 201. The proximal end of the treatment lumen 201 is sealed by means of a first backup member 203 and an O-ring 200 which are fixed to the fixing member 197 when a second backup member 198 is removed from the fixing member 197, the water feed and suction pipe 193 can be drawn out to the proximal side (in the axial direction).

At the proximal end of the endoscopic lumen 202, the fixing member 197 is fitted with the second backup member 198 which has an O-ring 199 in its bore. When the second backup member 198 is screwed into the fixing member 197, in this arrangement, the O-ring 199 is squeezed so that the endoscope 195 is fixed to the fixing member 197 in a sealed state.

The slide of the water feed and suction pipe 193 to the proximal end side is restrained as the first and second backup members 203 and 198 come into contact with each other. On the other hand, the slide of the pipe 193 to the distal end side is restrained as a proximal end portion 206 of the sheath and a projection 207, which is attached to the pipe 193 so as to project sideways from the treatment lumen 201, come into contact with each other.

A side hole 204 is formed in the distal end portion of the water feed and suction pipe 193. That portion of the pipe 193 which is situated on the distal end side of the hole 204 is partially constricted to form a recessed portion 205 with a reduced diameter. The recessed portion 205 allows a large quantity of water to be fed into the transparent cap 192 through the side hole 204, whereby an objective lens of the endoscope 195 can be washed.

According to the endoscopic sheath 190 constructed in this manner, as described above, the objective lens of the endoscope 195 and the transparent cap 192 can be washed with water which is fed into the cap 192 through the side hole 204 of the water feed and suction pipe 193 in case blood or the like gets into the cap 192 to block the view range of the endoscope 195 during a surgical operation. Thus, the view range can be maintained for smooth treatment at all times.

Since the recessed portion 205 at the distal end portion of the water feed and suction pipe 193 serves to increase the rate of water feed through the side hole 204, moreover, the objective lens of the endoscope 195 and the cap 192 can be washed securely and quickly.

In the endoscopic sheath 190 with the aforementioned construction, furthermore, the instrument, such as the water feed and suction pipe 193, is restrained from advancing and retreating or rotating, so that it cannot move unexpectedly. Thus, the instrument can be prevented from damaging tissue or projecting and hindering the surgical operation, so that the safety of the operation can be ensured.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An endoscopic sheath comprising:

a tubular sheath section including a distal end portion having an end which is entirely open except for a circumferential portion of the distal end portion, a proximal end portion, and a hole which extends through the sheath section such that an insert section of an endoscope having observation means can be passed from the proximal end portion through the hole to the distal end portion, and at least the distal end portion of the sheath section being formed of a transparent material; and positioning means for longitudinally positioning the distal end portion of the sheath section and a distal end portion of the insert section of the endoscope such that a direct image which passes through said end and an indirect image which passes through at least part of the distal end portion of the sheath section are within a same view range of the endoscope.

2. An endoscopic sheath according to claim 1, wherein said sheath section includes a tubular sheath body and a transparent cap attached to the sheath body, said transparent cap forming the distal end portion of the sheath section.

3. An endoscopic sheath according to claim 2, wherein said sheath body and said transparent cap are formed integrally with each other.

4. An endoscopic sheath according to claim 1, wherein said positioning means includes a stopper protruding from an inner surface of the distal end portion of the sheath section, said stopper being adapted to abut against a distal end face of the insert section of the endoscope.

5. An endoscopic sheath according to claim 4, wherein said positioning means includes a retaining means for maintaining abutment of the stopper against the distal end face of the insert section of the endoscope.

6. An endoscopic sheath according to claim 1, wherein said positioning means includes:

an engaging portion provided on the sheath section, a positioning member attached to the endoscope and having a plurality of engaged portions adapted to engage the engaging portion of the sheath section, the engaged portions of the positioning member being arranged adjacent to each other in a longitudinal direction of the endoscope, and disengaging means for disengaging the engaging portion of the sheath section and the engaged portions of the positioning member, whereby the insert section of the endoscope is positioned in the sheath section by changing the position of engagement between the engaging portion of the sheath section and the engaged portions of the positioning member by means of the disengaging means.

7. An endoscopic sheath according to claim 6, wherein: said engaging portion comprises a projection on the sheath section,

21 said positioning member includes an elongated engaging plate having a plurality of grooves thereon extending in a longitudinal direction thereof so as to engage the projection, and said disengaging means disengages the projection from the grooves of the engaging plate by deforming the projection.

8. An endoscopic sheath according to claim 1, wherein a distal end edge of said distal end portion of the sheath section is conically tapered.

9. An endoscopic sheath according to claim 1, wherein said sheath section includes a balloon provided on an outer peripheral surface of the sheath section for positioning the sheath section in a living body.

10. An endoscopic sheath according to claim 1, wherein said distal end portion comprises an aslant opening.

11. An endoscopic sheath according to claim 1, wherein said distal end portion includes a guide portion adapted to be guided by living tissue.

12. An endoscopic sheath according to claim 11, wherein said guide portion comprises a recessed groove formed on an outer peripheral surface of the distal end portion so as to extend in a longitudinal direction thereof, said recessed groove being adapted to engage the living tissue.

13. An endoscopic sheath according to claim 11, wherein said guide portion comprises a loop-shaped arm coupled to the distal end portion and adapted to catch the living tissue.

14. An endoscopic sheath according to claim 1, wherein said sheath section comprises a curl having a predetermined radius of curvature.

15. An endoscopic sheath according to claim 1, wherein said sheath section includes a plurality of lumina.

16. An endoscopic sheath according to claim 1, wherein said sheath section is provided with liquid feed means for feeding a liquid to the distal end of the sheath section.

17. An endoscopic sheath comprising:

a tubular sheath section having a distal end portion and a hole which extends through the sheath section such that an insert section of an endoscope having observation means can be passed through the hole, a distal end of the distal end portion being open, and at least the distal end portion being formed of a transparent material; and positioning means for positioning the insert section of the endoscope in the sheath aection such that at least part of the distal end portion of the sheath section is within a view range of the endoscope;

said distal end portion of the sheath including a guide portion adapted to be guided by living tissue, said guide portion comprising a recessed groove formed on an outer peripheral surface of the distal end portion of the sheath section so as to extend in a longitudinal direction thereof, and said recessed groove being adapted to engage the living tissue.

18. An endoscopic sheath comprising:

a tubular sheath section having a distal end portion and a hole which extends through the sheath section such that an insert section of an endoscope having observation means can be passed through the hole, a distal end of the distal end portion being open, and at least the distal end portion being formed of a transparent material; and positioning means for positioning the insert section of the endoscope in the sheath section such that at least part of the distal end portion of the sheath section is within a view range of the endoscope;

said distal end portion of the sheath including a guide portion adapted to be guided by living tissue, said guide portion comprising a loop-shaped arm coupled to the distal end portion and adapted to catch the living tissue.

19. An endoscopic sheath comprising:

a tubular sheath section having a distal end portion, a proximal portion and a hole which extends through the sheath section such that an insert section of an endoscope having observation means can be passed from the proximal end portion through the hole to the distal end portion, a distal end of the distal end portion being open, and at least the distal end portion being formed of a transparent material;

positioning means for longitudinally positioning the distal end portion of the sheath section and a distal end portion of the insert section of the endoscope such that at least part of the distal end portion of the sheath section is within a view range of the endoscope; and said sheath section including a tubular sheath body and a transparent cap attached to the sheath body, said transparent cap forming the distal end portion of the sheath section, and said sheath body and said transparent cap are formed integrally with each other.

20. An endoscopic sheath comprising:

a tubular sheath section having a distal end portion, a proximal portion and a hole which extends through the sheath section such that an insert section of an endoscope having observation means can be passed from the proximal end portion through the hole to the distal end portion, a distal end of the distal end portion being open, and at least the distal end portion being formed of a transparent material; and positioning means for longitudinally positioning the distal end portion of the sheath section and a distal end portion of the insert section of the endoscope such that at least part of the distal end portion of the sheath section is within a view range of the endoscope, said positioning means including a stopper protruding from an inner surface of the distal end portion of the sheath section, said stopper being adapted to abut against a distal end face of the insert section of the endoscope.

21. An endoscopic sheath according to claim 20, wherein said positioning means includes a retaining means for maintaining abutment of the stopper against the distal end face of the insert section of the endoscope.

22. An endoscopic sheath comprising:

a tubular sheath section having a distal end portion, a proximal portion and a hole which extends through the sheath section such that an insert section of an endoscope having observation means can be passed from the proximal end portion through the hole to the distal end portion, a distal end of the distal end portion being open, and at least the distal end portion being formed of a transparent material; and positioning means for longitudinally positioning the distal end portion of the sheath section and a distal end portion of the insert section of the endoscope such that at least part of the distal end portion of the sheath section is within a view range of the endoscope, said positioning means including:

an engaging portion provided on the sheath section, a positioning member attached to the endoscope and having a plurality of engaged portions adapted to engage the engaging portion of the sheath section, the engaged portions of the positioning member being arranged adjacent to each other in a longitudinal direction of the endoscope, and disengaging means for disengaging the engaging portion of the sheath section and the engaged portions of the positioning member, whereby the insert section of the endoscope is positioned in the sheath section by changing the position of engagement between the engaging portion of the sheath section and the engaged portions of the positioning member by means of the disengaging means.

23. An endoscopic sheath according to claim 22, wherein:

said engaging portion comprises a projection on the sheath section, said positioning member includes an elongated engaging plate having a plurality of grooves thereon extending in a longitudinal direction thereof so as to engage the projection, and said disengaging means disengages the projection from the grooves of the engaging plate by deforming the projection.

24. An endoscopic sheath comprising:

a tubular sheath section having a distal end portion, a proximal portion and a hole which extends through the sheath section such that an insert section of an endoscope having observation means can be passed from the proximal end portion through the hole to the distal end portion, a distal end of the distal end portion being open, at least the distal end portion being formed of a transparent material, and a distal end edge of said distal end portion of the sheath section is conically tapered; and positioning means for longitudinally positioning the distal end portion of the sheath section and a distal end portion of the insert section of the endoscope such that at least part of the distal end portion of the sheath section is within a view range of the endoscope.

25. An endoscopic sheath comprising:

a tubular sheath section having a distal end portion, a proximal portion and a hole which extends through the sheath section such that an insert section of an endoscope having observation means can be passed from the proximal end portion through the hole to the distal end portion, a distal end of the distal end portion being open, at least the distal end portion being formed of a transparent material, and said sheath section includes a balloon provided on an outer peripheral surface of the sheath section for positioning the sheath section in a living body; and positioning means for longitudinally positioning the distal end portion of the sheath section and a distal end portion of the insert section of the endoscope such that at least part of the distal end portion of the sheath section is within a view range of the endoscope.

26. An endoscopic sheath comprising:

a tubular sheath section having a distal end portion, a proximal portion and a hole which extends through the sheath section such that an insert section of an endoscope having observation means can be passed from the proximal end portion through the hole to the distal end portion, a distal end of the distal end portion being open, at least the distal end portion being formed of a transparent material, and said distal end portion comprises an aslant opening; and positioning means for longitudinally positioning the distal end portion of the sheath section and a distal end portion of the insert section of the endoscope such that at least part of the distal end portion of the sheath section is within a view range of the endoscope.

27. An endoscopic sheath comprising:

a tubular sheath section having a distal end portion, a proximal portion and a hole which extends through the sheath section such that an insert section of an endoscope having observation means can be passed from the proximal end portion through the hole to the distal end portion, a distal end of the distal end portion being open, at least the distal end portion being formed of a transparent material, and said distal end portion includes a guide portion adapted to be guided by living tissue; and positioning means for longitudinally positioning the distal end portion of the sheath section and a distal end portion of the insert section of the endoscope such that at least part of the distal end portion of the sheath section is within a view range of the endoscope.

28. An endoscopic sheath according to claim 27, wherein said guide portion comprises a recessed groove formed on an outer peripheral surface of the distal end portion so as to extend in a longitudinal direction thereof, said recessed groove being adapted to engage the living tissue.

29. An endoscopic sheath according to claim 27, wherein said guide portion comprises a loop-shaped arm coupled to the distal end portion and adapted to catch the living tissue.

30. An endoscopic sheath comprising:

a tubular sheath section having a distal end portion, a proximal portion and a hole which extends through the sheath section such that an insert section of an endoscope having observation means can be passed from the proximal end portion through the hole to the distal end portion, a distal end of the distal end portion being open, at least the distal end portion being formed of a transparent material, and said sheath section comprises a curl having a predetermined radius of curvature; and positioning means for longitudinally positioning the distal end portion of the sheath section and a distal end portion of the insert section of the endoscope such that at least part of the distal end portion of the sheath section is within a view range of the endoscope.

31. An endoscopic sheath comprising:

a tubular sheath section having a distal end portion, a proximal portion and a hole which extends through the sheath section such that an insert section of an endoscope having observation means can be passed from the proximal end portion through the hole to the distal end portion, a distal end of the distal end portion being open, at least the distal end portion being formed of a transparent material, and said sheath section includes a plurality of lumina; and positioning means for longitudinally positioning the distal end portion of the sheath section and a distal end portion of the insert section of the endoscope such that at least part of the distal end portion of the sheath section is within a view range of the endoscope.

* * * * *